US009259359B2

(12) United States Patent
Fujita

(10) Patent No.: US 9,259,359 B2
(45) Date of Patent: Feb. 16, 2016

(54) FOLDING DEVICE, FOLDING SYSTEM, AND FOLDING METHOD FOR DISPOSABLE WORN ARTICLE

(75) Inventor: Yukihiko Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 581 days.

(21) Appl. No.: 13/639,356

(22) PCT Filed: May 30, 2011

(86) PCT No.: PCT/JP2011/062364
§ 371 (c)(1),
(2), (4) Date: Oct. 4, 2012

(87) PCT Pub. No.: WO2011/152346
PCT Pub. Date: Dec. 8, 2011

(65) Prior Publication Data
US 2013/0029827 A1 Jan. 31, 2013

(30) Foreign Application Priority Data

Jun. 4, 2010 (JP) ................................ 2010-128724

(51) Int. Cl.
A61F 13/15 (2006.01)

(52) U.S. Cl.
CPC ..... A61F 13/15585 (2013.01); A61F 13/15747 (2013.01)

(58) Field of Classification Search
CPC ............ A61F 13/15747; A61F 13/496; A61F 13/55115; A61F 13/15577; A61F 13/15682
USPC ........ 493/357, 437, 359, 454, 360, 436, 442, 493/450, 405; 156/73.1, 163, 164, 217, 156/226, 227, 264, 269, 308.4, 443, 538, 156/539, 543, 566, 580.1
See application file for complete search history.

(56) References Cited

U.S. PATENT DOCUMENTS 5,080,741 A * 1/1992 Nomura ............ A61F 13/15593
156/201
5,779,831 A * 7/1998 Schmitz ............ A61F 13/15707
156/163

(Continued)

FOREIGN PATENT DOCUMENTS

JP 07-205943 A 8/1995
JP 10-511292 A 11/1998

(Continued)

OTHER PUBLICATIONS

International Search Report for corresponding International Application No. PCT/JP2011/062364 mailed Aug. 30, 2011.

Primary Examiner — Andrew M Tecco
Assistant Examiner — Chelsea Stinson
(74) Attorney, Agent, or Firm — Renner, Otto, Boisselle & Sklar, LLP

(57) ABSTRACT

A device including: a main folding mechanism for folding a diaper body in two at the crotch portion by rotating first and second main pads having first and second holding surfaces, respectively; and a sub-folding mechanism for folding the flap by rotating a side pad having a sub-holding surface for holding the flap with respect to the first main pad, wherein; a cut-out is formed at a position corresponding to the attachment portion of the second main pad, wherein the cut-out does not allow the attachment portion to be held by the second main pad but instead expose the attachment portion; with the first and second holding surfaces being closed while opposing each other and with the main body folded in two, the cut-out allows the flap to be attached to the attachment portion; and the side pad rotates from a position where it is open while lying next to the first main pad in the girth direction to a position where the sub-holding surface is closed while opposing the first holding surface, fitting into the cut-out.

11 Claims, 20 Drawing Sheets

(56) References Cited

U.S. PATENT DOCUMENTS

| | | | | |
|---|---|---|---|---|
| 6,565,691 B2* | 5/2003 | Tomsovic | A61F 13/15699 | 156/202 |
| 7,008,497 B2* | 3/2006 | Nakakado | A61F 13/15593 | 156/160 |
| 7,322,925 B2* | 1/2008 | Couillard | A61F 13/15772 | 493/394 |
| 7,335,150 B2* | 2/2008 | Coenen | A61F 13/15707 | 493/256 |
| 8,225,837 B2* | 7/2012 | Schneider | A61F 13/15747 | 156/443 |
| 8,556,790 B2* | 10/2013 | Fujita | A61F 13/15747 | 493/357 |
| 8,821,360 B2* | 9/2014 | Umebayashi | A61F 13/15756 | 493/405 |
| 8,939,876 B2* | 1/2015 | Schneider | A61F 13/15756 | 156/258 |
| 8,940,118 B2* | 1/2015 | Schneider | A61F 13/15747 | 156/227 |
| 2003/0111168 A1* | 6/2003 | Olson | A61F 13/15747 | 156/250 |
| 2004/0106506 A1 | 6/2004 | Ninomiya et al. | | |
| 2007/0137011 A1 | 6/2007 | Couillard et al. | | |
| 2008/0083489 A1* | 4/2008 | Schneider | A61F 13/15739 | 156/258 |
| 2011/0287919 A1 | 11/2011 | Umebayashi | | |
| 2011/0319243 A1 | 12/2011 | Fujita | | |

FOREIGN PATENT DOCUMENTS

| | | |
|---|---|---|
| JP | 2002-087695 A | 3/2002 |
| JP | 2002-355270 A | 12/2002 |
| JP | 2005-000296 A | 1/2005 |
| JP | 2005-534348 A | 11/2005 |
| JP | 2009-519744 A | 5/2009 |
| WO | 2010/089964 A1 | 8/2010 |
| WO | 2010/119884 A1 | 10/2010 |

* cited by examiner

FOLDING DEVICE, FOLDING SYSTEM, AND FOLDING METHOD FOR DISPOSABLE WORN ARTICLE

TECHNICAL FIELD

The present invention relates to a folding device, a folding system and a folding method for disposable worn articles.

BACKGROUND ART

Devices and methods have been provided in the art for folding in two a crotch portion of a disposable worn article such as a diaper (the first and second patent documents).

CITATION LIST

Patent Literature

[First Patent Document] Japanese Laid-Open Patent Publication No. 7-205943
[Second Patent Document] Japanese National Phase PCT Laid-Open Publication No. 2009-519744

SUMMARY OF INVENTION

Technical Problem

However, the documents cited above fail to disclose a technique for folding flaps of a diaper.

It is therefore an object of the present invention to provide a folding device, a folding system and a folding method, with which it is possible to fold a disposable worn article at the crotch portion and to fold flaps thereof.

Solution to Problem

In order to achieve the object set forth above, a folding device of the present invention is a folding device for a disposable worn article, the disposable worn article including: a main body including a first torso portion covering a portion of a torso of a wearer, a second torso portion covering another portion of the torso of the wearer and a crotch portion covering a crotch of the wearer, which are continuous with one another in a longitudinal direction; and a flap being continuous with an edge portion of the first torso portion extending in the longitudinal direction and extending from the edge portion in a girth direction perpendicular to the longitudinal direction so as to be attached to an attachment portion of a non-skin-contact surface of the second torso portion, the folding device including: a first main pad having a first holding surface for holding the first torso portion; a second main pad having a second holding surface for holding a portion of the second torso portion with the attachment portion being not held but exposed; a main folding mechanism for folding the main body in two at the crotch portion by rotating the first main pad and the second main pad relative to each other so as to transition from a main open state in which the first main pad and the second main pad are open while lying next to each other in the longitudinal direction to a main closed state in which the first holding surface and the second holding surface are closed while opposing each other; a side pad having a sub-holding surface for holding the flap; and a sub-folding mechanism for folding the flap so that a skin-contact surface of the flap lies on the attachment portion of the non-skin-contact surface of the second torso portion by rotating the side pad with respect to the first main pad from a sub-open position in which the side pad is open while lying next to the first main pad in the girth direction to a sub-closed position in which the sub-holding surface is closed while opposing the first holding surface, wherein: a cut-out is formed at a position of the second main pad corresponding to the attachment portion, wherein the cut-out does not allow the attachment portion to be held by the second main pad but instead expose the attachment portion; in the main closed state and with the main body folded in two at the crotch portion, the cut-out allows the flap to be attached to the attachment portion of the second torso portion, and the side pad rotates from the sub-open position to the sub-closed position, fitting into the cut-out.

The worn article is folded as follows, for example, by the present folding device.

First, the first torso portion is held by a first main pad; the second torso portion is held by a second main pad with the attachment portion being not held but exposed; and the flap is held by a side pad.

Then, the main body is folded at the crotch portion by rotating at least one of the first main pad and the second main pad, with the attachment portion of the second torso portion being not held by the second main pad but exposed, and so that a skin-contact surface of the first torso portion and a skin-contact surface of the second torso portion lie on each other and are in contact with each other.

Immediately before or immediately after the completion of the folding of the main body or simultaneously with the completion of the folding of the main body, a skin-contact surface of the flap is folded onto the attachment portion by rotating the side pad holding the flap with respect to the first main pad toward the exposed attachment portion, with the attachment portion of the second torso portion being not held by the second main pad but exposed and with the main body folded at the crotch portion by the main pads.

Advantageous Effects of Invention

When the flap is folded onto the attachment portion of the second torso portion, the side pad holding a portion of the flap corresponding to the attachment portion fits into the cut-out area formed in the second main pad, whereby the side pad rotates from the sub-open position to the sub-closed position, fitting into the cut-out.

Thus, the flap can be folded.

DESCRIPTION OF EMBODIMENTS

Figure 1:
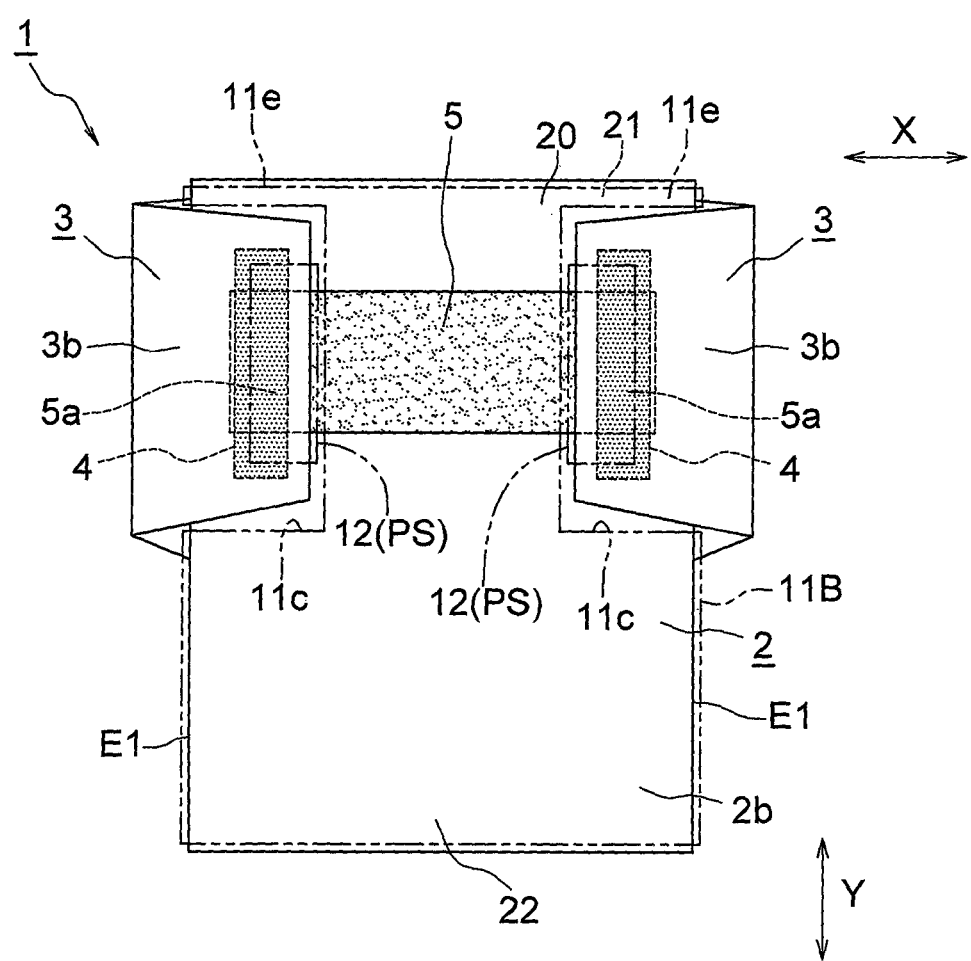
FIG. 1 is a schematic plan view showing a diaper folded by a folding device and method of the present invention.

In a preferred embodiment of the present invention, the main folding mechanism rotates the second main pad with respect to the first main pad from the main open state to a position where the second holding surface opposes the first holding surface and a portion of the second holding surface is generally parallel to a portion of the first holding surface.

Since the second main pad is rotated with respect to the first main pad, it is not necessary to rotate the first main pad, which is holding the first torso portion from which the flap is extended. This simplifies the structure of the sub-folding mechanism for the side pad which rotates with respect to the first main pad.

The rotation is done to a position (the squarely-opposing position) where the second holding surface opposes, and is parallel to, the first holding surface, i.e., the second holding surface squarely opposes the first holding surface, thereby allowing for more accurate folding of the main body.

In this case, a preferred main folding mechanism includes: arms each rotating about a first axis, a wrist for rotatably supporting, in a tip portion of each arm, the second main pad about a second axis parallel to the first axis, and a main driving mechanism for rotating the arm and the wrist in a predetermined rotation direction in order to fold the main body.

According to this aspect, the second main pad is rotatably supported via both the arm and the wrist, thereby allowing the second holding surface of the second main pad to squarely oppose the first holding surface.

A more preferred folding system of the present invention is a folding system including a plurality of folding devices provided on a drum rotating about a main rotation shaft, wherein the first holding surface is provided along a conveyance circle centered about the main rotation shaft, the main driving mechanism including: an arm rotating mechanism for rotating the arm about the first axis so that the second main pad moves from a first position where the second main pad is lying next to the first main pad to a second position where the second main pad is on a circumferentially outer side of the first main pad, as the first holding surface rotates on the conveyance circle following the rotation of the main rotation shaft; and a wrist rotating mechanism for rotating the second main pad on the wrist about the second axis following the rotation of the arm by the arm rotating mechanism.

In this case, the second main pad rotates about the wrist while revolving together with the arm, and smooth folding on the drum can therefore be expected.

Another preferred folding system of the present invention is a folding system including a plurality of folding devices along an outer periphery of a drum rotating about a main rotation shaft, the folding system including: a first cam provided on a side surface of the drum; a first cam follower guided along the first cam; and a main driving mechanism for driving the main folding mechanism as the first cam follower circles along the first cam.

In this case, it is possible to fold main bodies and flaps of worn articles on a single drum, thereby realizing a compact system.

In a more preferred folding system of the present invention, a pair of the side pads and a pair of the sub-folding mechanisms are provided for each first main pad, wherein the folding system includes: a pair of second cams provided on the outer periphery surface of the drum; second cam followers guided along the second cams; and a sub-driving mechanism for driving each of the sub-folding mechanisms as each of the second cam followers circle along each of the second cams.

Where pairs of sub-folding mechanisms are provided on a drum, the structure will likely be complicated if the cams are provided on the side surface of the drum.

In contrast, as pairs of cams and cam followers are provided each in symmetric fashion along the circumferential surface of the drum, the structure of the pair of sub-folding mechanisms becomes simple.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

EMBODIMENTS

An embodiment of the present invention will now be described with reference to FIGS. 1 to 20.

Diaper 1:

As shown in FIG. 1, a diaper 1 of the present embodiment includes a diaper main body 2, and a pair of flaps 3. The diaper main body 2 includes a front portion (second torso portion) 20 covering a front torso of the wearer, a back portion (first torso portion) 21 covering a back torso of the wearer, and a crotch portion 22 covering the crotch between the front portion 20 and the back portion 21.

Figure 2B:
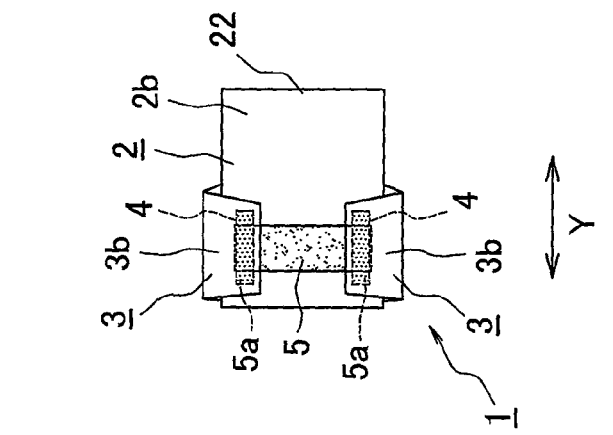
FIGS. 2A and 2B are schematic front views showing a folding method for the diaper.
Figure 2A:
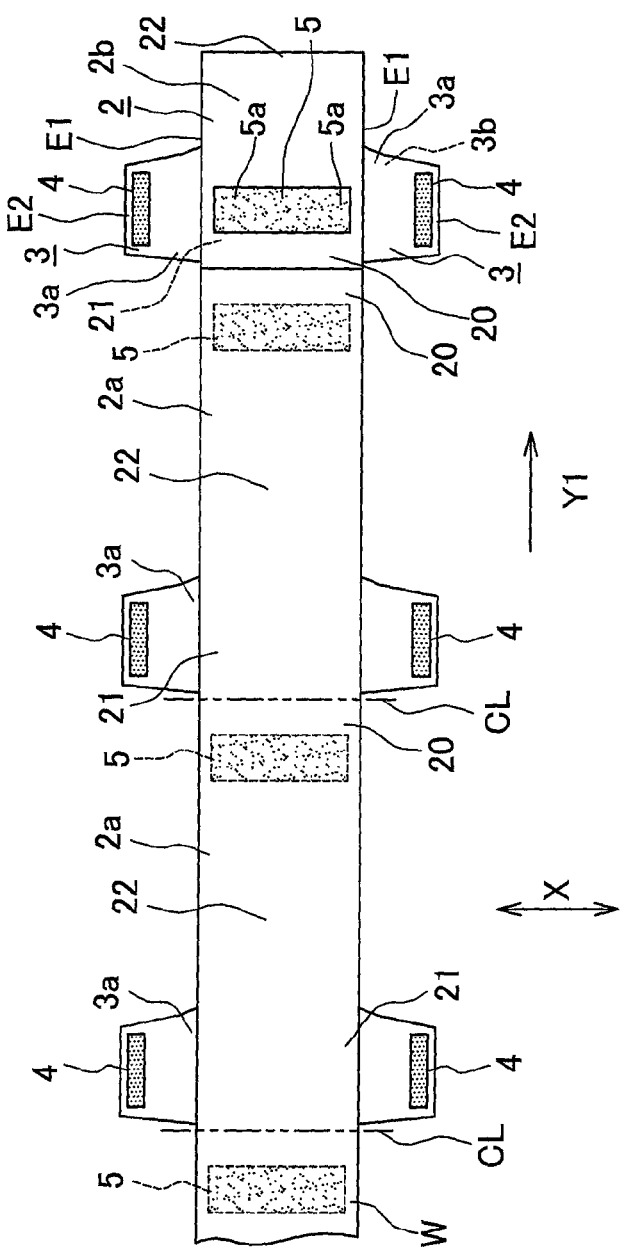

As shown in FIG. 2A, each flap 3 extends in the girth direction X from an edge portion E1 of the diaper main body 2 in the longitudinal direction Y.

A first fastener member formed by a male touch fastener 4 is fixed to a skin-contact surface 3a of an end portion E2 of each flap 3 in the girth direction X.

On the other hand, a second fastener member formed by a female touch fastener 5 is provided on a non-skin-contact surface 2b of the front portion 20 of FIG. 1. As shown in the figure, the male touch fastener 4 engages with the female touch fastener 5. A portion of the female touch fastener 5 forms an attachment portion 5a to which the flaps 3 are attached.

Note that where the non-skin-contact surface 2b of the diaper main body 2 is formed by a non-woven fabric, the second fastener member may be formed by the non-woven fabric.

The term "skin-contact surface" as used herein refers to the surface which directly or indirectly faces the skin surface of the wearer when the diaper 1 is worn, and the "non-skin-contact surface" refers to the surface opposite to the skin-contact surface.

An adsorbent body (not shown) is provided on the diaper main body 2.

Three-dimensional gathers may be provided on the diaper main body 2.

The diaper main body 2 may include around-leg portions which have been cut so as to conform to the legs of the wearer. Elastic members formed by rubber threads, or the like, for example, may be provided so as to conform to the legs of the wearer in the around-leg portion or portions of the flaps 3 that are connected to the around-leg portions.

Moreover, an elastic member for fitting the diaper 1 to the wearer may be provided in portions of the front portion 20 and the back portion 21 of the diaper main body 2 which are to be present around the torso and in the flaps 3. The elastic member may be, for example, a plurality of rubber threads or rubber tapes, a material including a film or a thermoplastic resin, or the like.

A laminated web W to be the diaper 1 is folded in two in the crotch portion 22 as shown in FIG. 2A, and is folded so that the skin-contact surface 2a of the back portion 21 and the skin-contact surface 2a of the front portion 20 lie on each other. As shown in FIGS. 2A and 2B, the skin-contact surface 3a of the flap 3 is folded toward the female touch fastener 5 of the front portion 20 of the diaper main body 2, and the diaper 1 is shipped with the set of fasteners 4 and 5 engaged with each other and pair of flaps 3 fastened to the diaper main body 2.

When wearing the diaper 1 of FIG. 1, a wearer puts it on as if it were a pants-type diaper, with the flaps 3 fastened to the diaper main body 2. On the other hand, if the diaper 1 does not sufficiently fit to the wearer, the male touch fasteners 4 of the flaps 3 may be once taken off the female touch fastener 5 of the diaper main body 2, and the male touch fasteners 4 may be re-fastened to the female touch fastener 5, thereby fitting the diaper 1 to the wearer.

Folding System:

Next, a folding system for severing the laminated web W and folding the main body 2 and the flaps 3 as shown in FIGS. 2A and 2B will be described.

Figure 3:
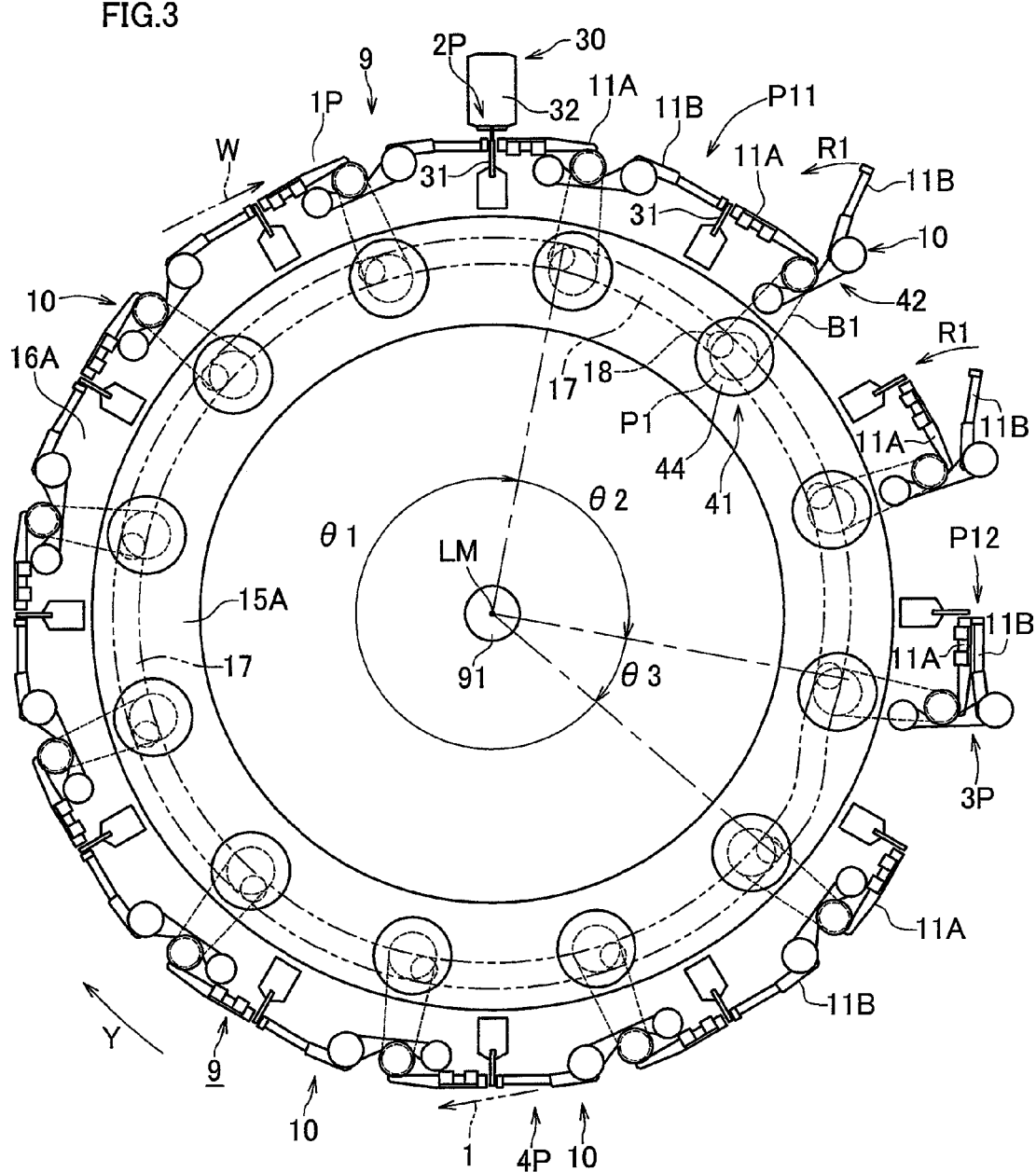
FIG. 3 is a schematic side view showing a folding system for the diaper.

As shown in FIG. 3, this folding system includes a folding drum 9. A cutter roller 30 is arranged so as to oppose the folding drum 9.

The folding drum 9 includes a plurality of sets of folding units 10 rotating about a main rotation shaft 91. As is well known in the art, the folding drum 9 includes a fixed portion 15A fixed to a fixed frame rotatably supporting the main rotation shaft 91 of FIGS. 3 and 20, and rotating portions 16A and 16B rotatably supported about the fixed portion 15A. A torque from a motor (not shown) is input to the main rotation shaft 91, and the rotating portions 16A and 16B rotate about the main axis LM following the rotation of the main rotation shaft 91.

Figure 4:
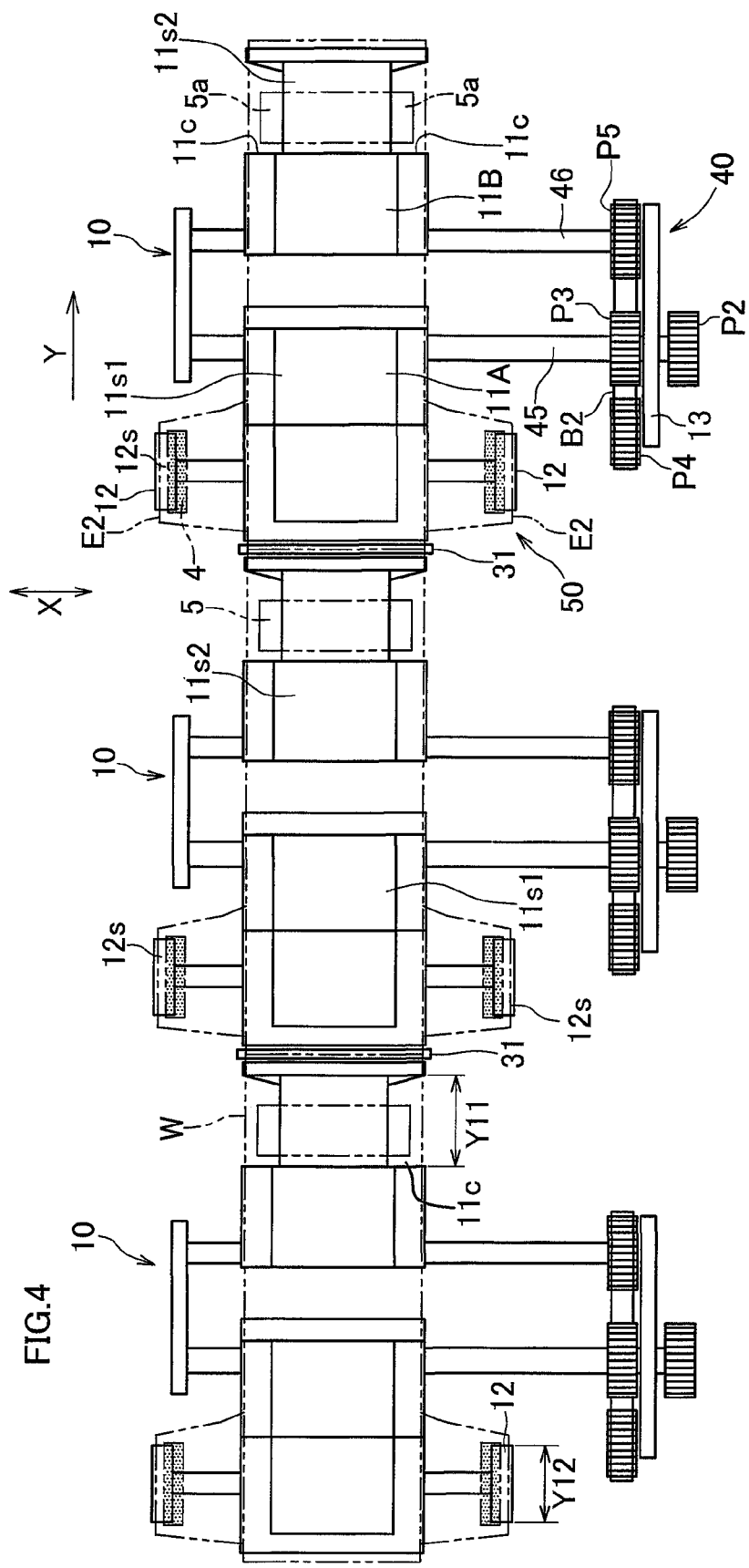
FIG. 4 is a schematic plan view showing a part of a folding system for the diaper.
Figure 11:
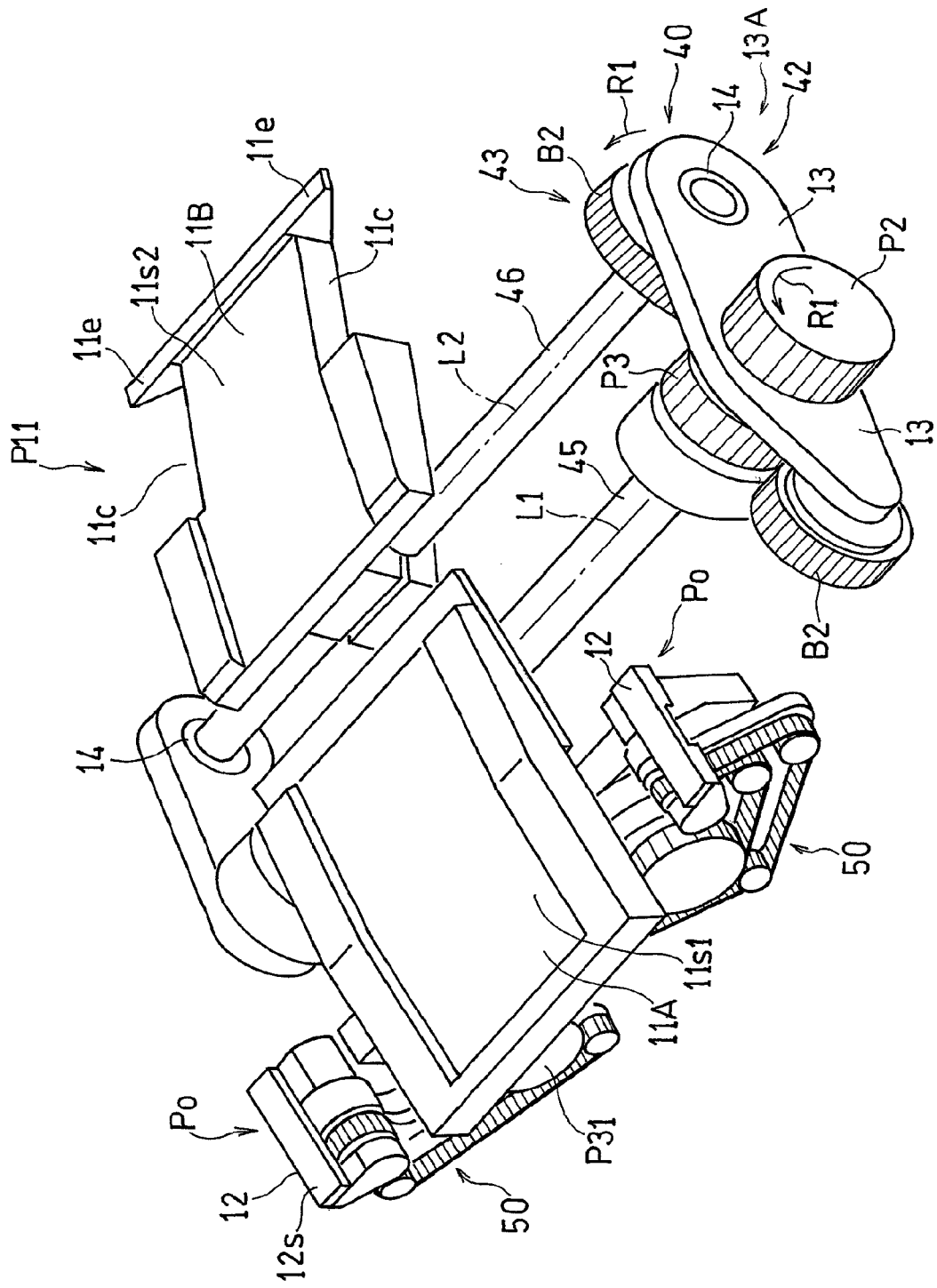
FIG. 11 is a schematic perspective view showing a folding device in a main open state.

As shown in FIGS. 4 and 11, each folding unit 10 includes an anvil 31 (FIG. 4), a main pad 11, a pair of side pads 12, a main folding mechanism 40, and a sub-folding mechanism 50. The main pad 11 includes a first main pad 11A and a second main pad 11B, and the term "the main pad 11" will be used hereinafter to collectively refer to both of the main pads 11A and 11B.

Figure 20:
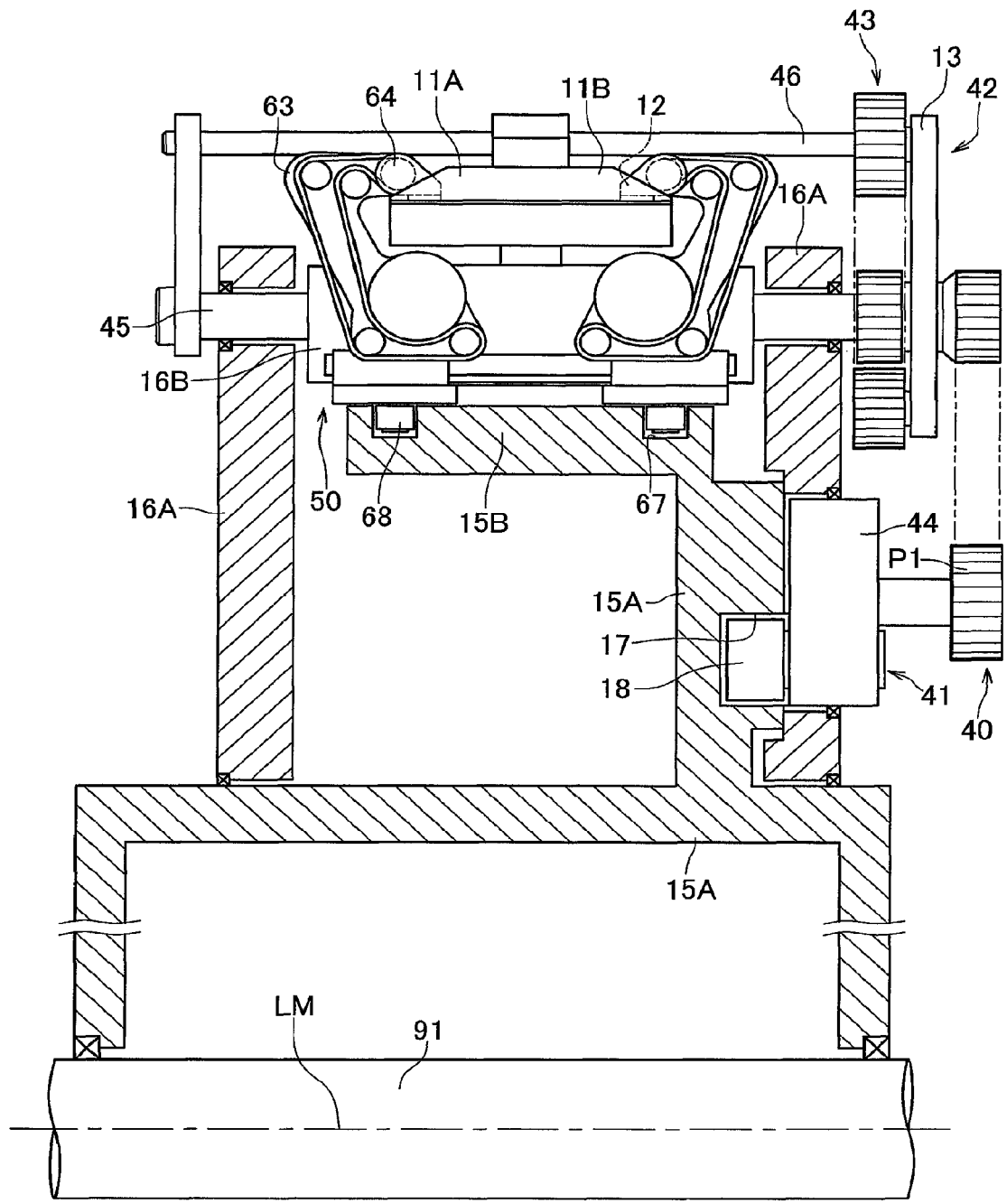
FIG. 20 is a schematic cross-sectional view showing the folding device in a main closed state, where side pads are in a sub-closed position.

Each folding unit 10 including the anvil 31 (FIG. 4), the main pad 11, the side pad 12 and the folding mechanisms 40 and 50 is attached to the rotating portion 16B shown in FIG. 20, and rotates about the main axis LM together with the rotating portion 16B following the rotation of the main rotation shaft 91.

Figure 5:
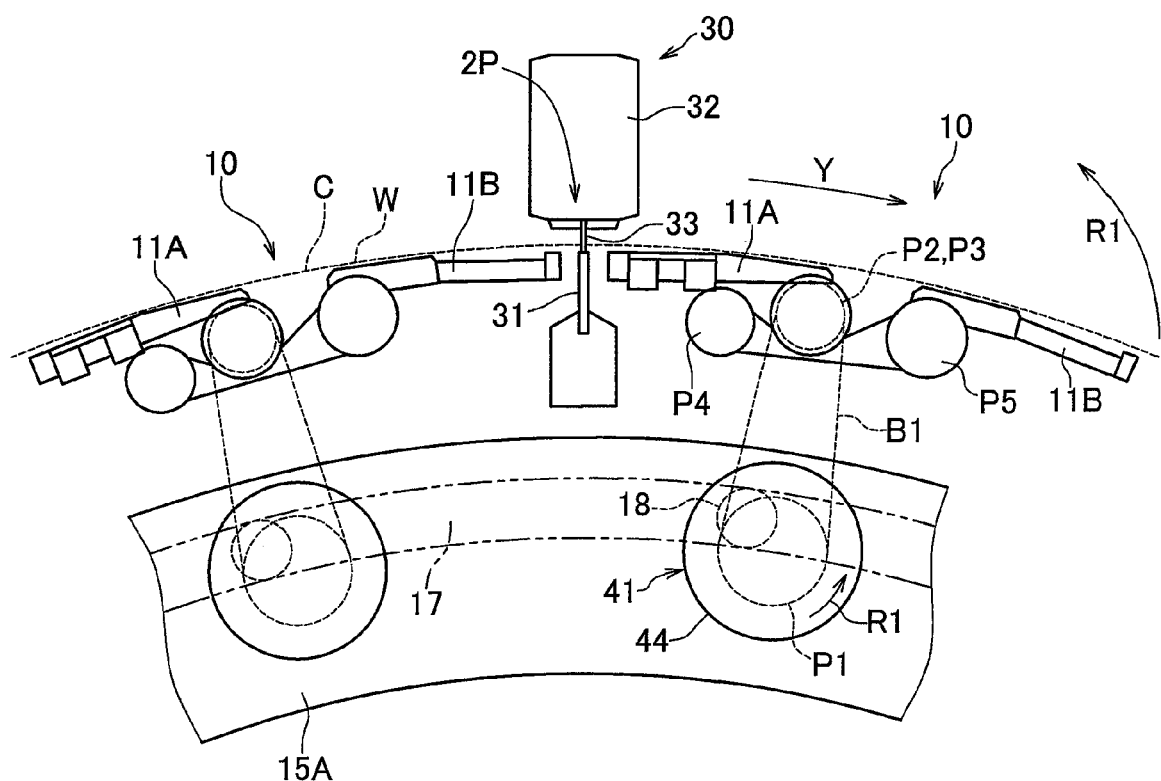
FIG. 5 is a schematic side view showing the vicinity of a cutter of the folding system.

As shown in FIG. 5, the anvil 31 forms a severing device 30 together with a cutter roller 32 and a blade 33.

The severing device 30 of FIG. 3 severs the web W into individual diapers downstream of the pickup position 1P (FIG. 3) of the web W.

As shown in FIG. 3, in this folding system, the main pad 11 (11A, 11B) and the side pad 12 (FIG. 4) pick up the web W to be the diaper 1 at the pickup position 1P upstream of the folding position 3P where the folding is done. The main pad 11 (11A, 11B) hands over the diaper 1 to a downstream conveyer device (not shown) at the hand-over position 4P downstream of the folding position 3P. The folding position 3P is located downstream of the severing position 2P.

The main pad 11 (11A, 11B) receives at least the main body 2 on first and second holding surfaces $11s1$ and $11s2$ (FIG. 11) which are provided along the conveyance circle C (FIG. 5) about the main rotation shaft 91. The main pad 11 moves along the conveyance circle C following the rotation of the main rotation shaft 91 while holding the main body 2 on the first and second holding surfaces $11s1$ and $11s2$.

Figure 15:
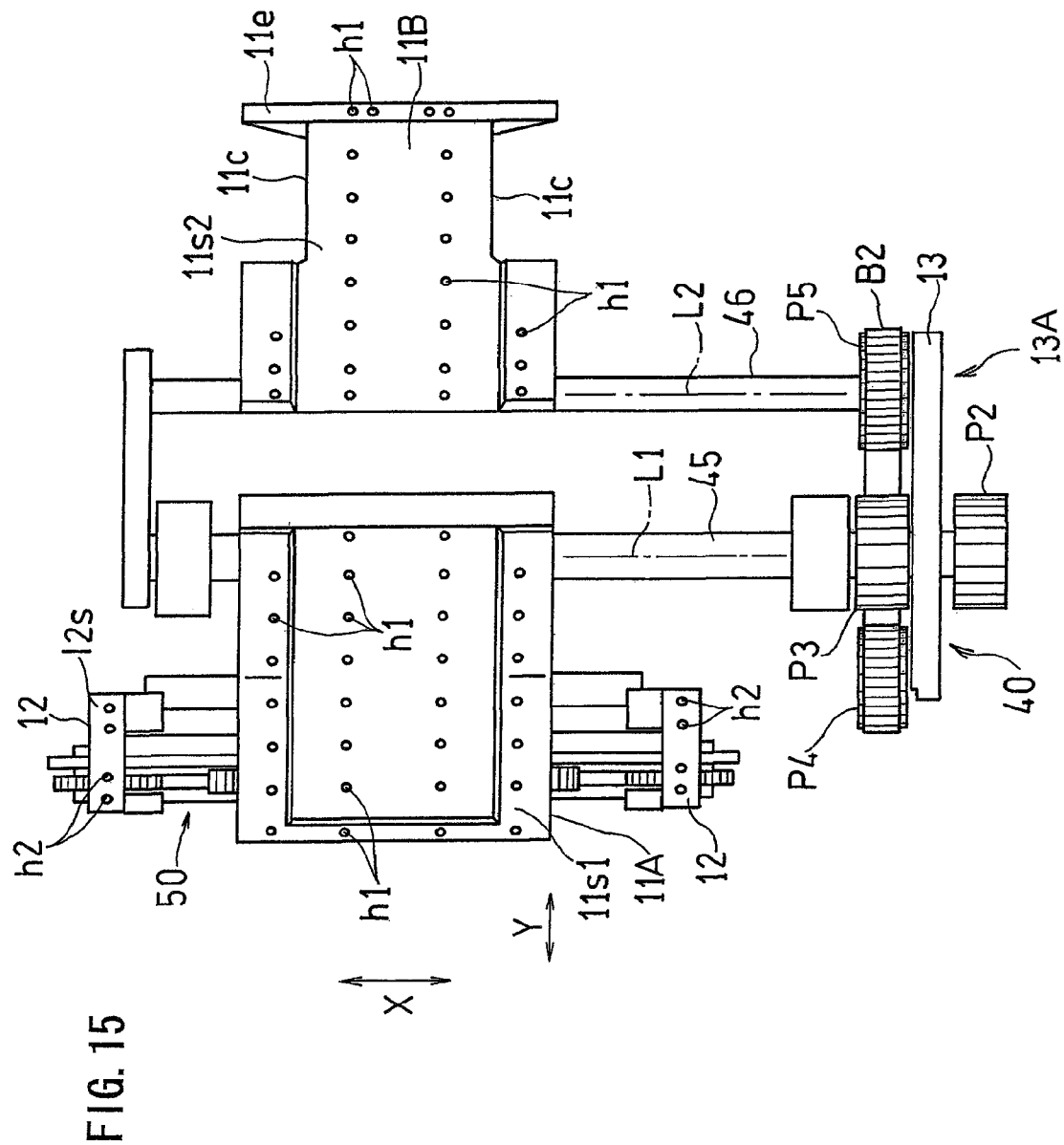
FIG. 15 is a schematic plan view showing a folding device.

As shown in FIG. 15, a large number of air holes h1 are open on the first and second holding surfaces $11s1$ and $11s2$ for holding the main body 2 through suction by a negative pressure, for example.

Figure 6:
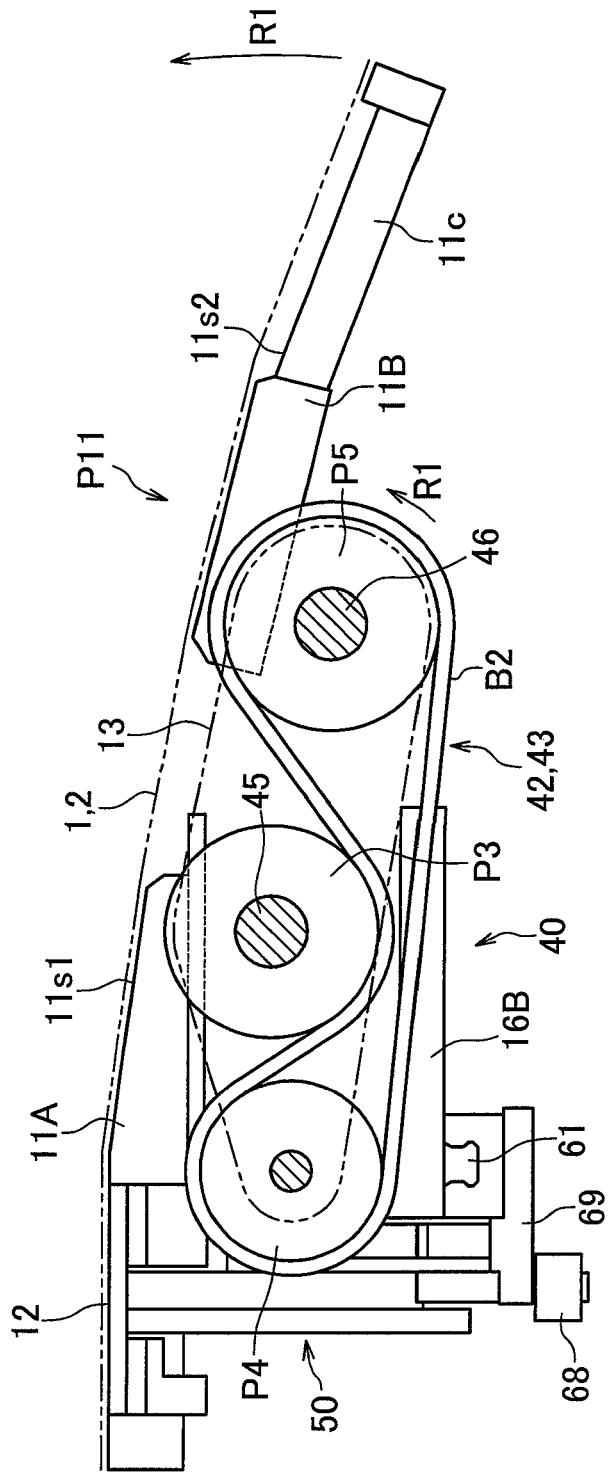
FIG. 6 is a partially-cross-sectional schematic side view showing the folding device in a main open state.

As shown in FIGS. 4 to 6, the first main pad 11A includes the first holding surface $11s1$ which holds the back portion 21 (FIG. 2A). On the other hand, the second main pad 11B includes the second holding surface $11s2$ for holding a portion of the front portion 20 (FIG. 2A) with the attachment portion $5a$ being not held but exposed.

The holding surfaces $11s1$ and $11s2$ of the main pad 11 (11A, 11B) include depressions/protrusions in accordance with the thickness of the diaper main body 2. The first main pad 11A and the second main pad 11B are spaced apart from each other in the longitudinal direction Y, thereby making easy the folding at the crotch portion 22 as shown in FIG. 8.

Figure 7:
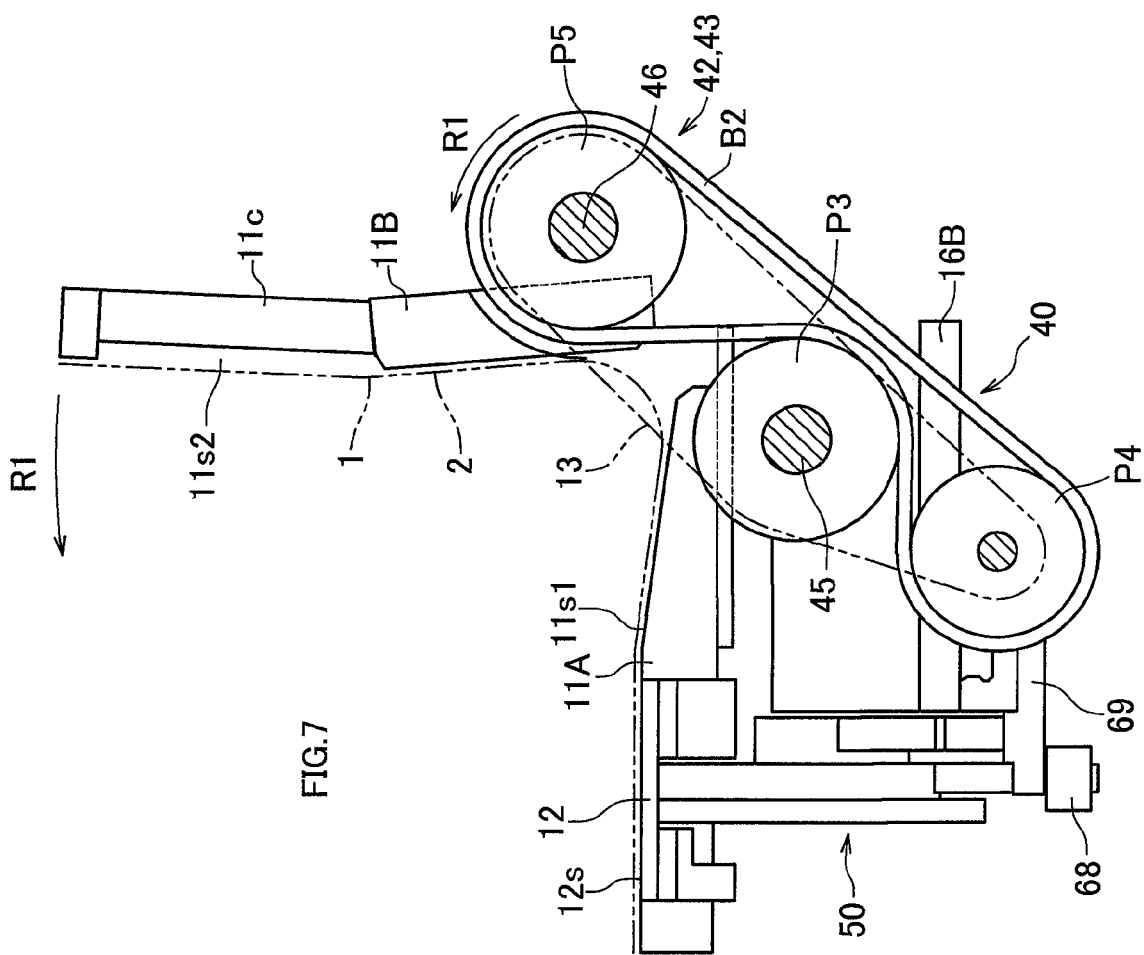
FIG. 7 is a schematic side view showing the folding device in a half open state.
Figure 8:
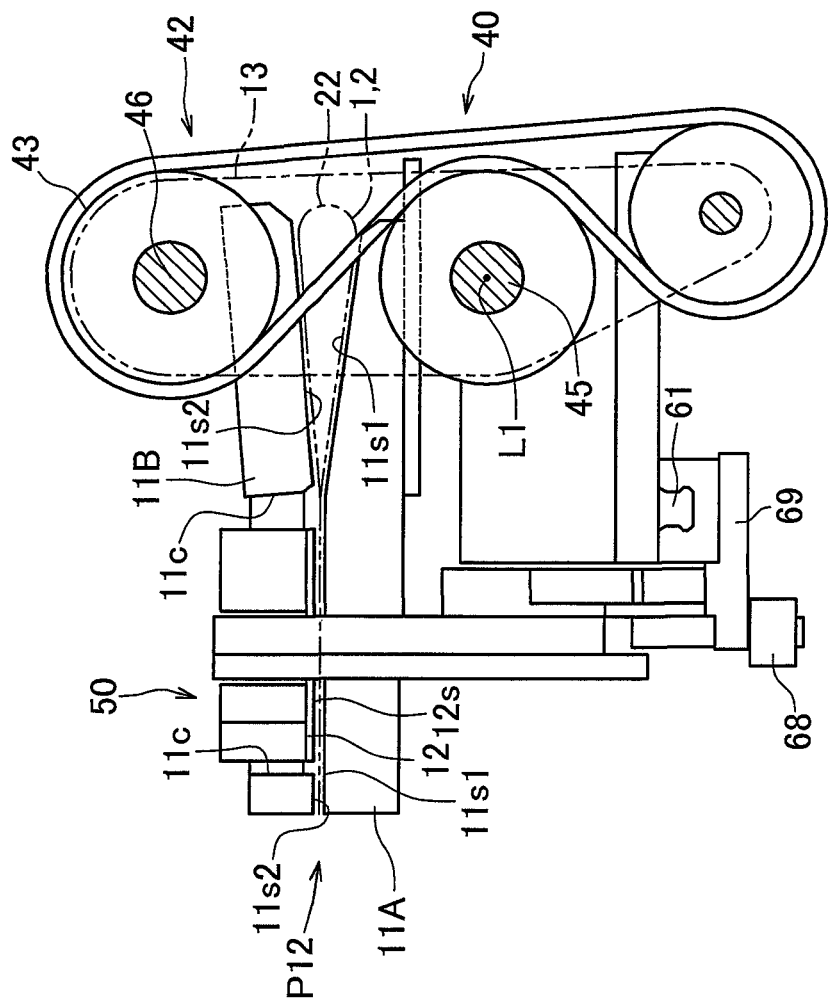
FIG. 8 is a schematic side view showing the folding device in a main closed state.

As shown in FIGS. 6 to 8 and 11 to 14, the main folding mechanism 40 folds the diaper main body 2 in two at the crotch portion 22 by rotating the second main pad 11B with respect to the first main pad 11A so as to transition from the main open state in which the first main pad 11A and the second main pad 11B of FIG. 6 are open while lying next to each other in the longitudinal direction Y to the main closed state in which the first holding surface $11s1$ and the second holding surface $11s2$ of FIG. 8 are closed while opposing each other.

As shown in FIG. 4, a pair of side pads 12 are arranged on the first main pad 11A along the conveyance circle C (FIG. 5) of the first main pad 11A. As shown in FIG. 4, the side pad 12 receives at least the end portion E2 in the girth direction X of the flap 3 on the sub-holding surface $12s$ provided along the conveyance circle C (FIG. 5). The end portion E2 of the flap 3 is sucked and held on the sub-holding surface $12s$.

A plurality of air holes h2 of FIG. 15 are open in a sub-holding surface $12s$ for holding the flaps 3 through suction by a negative pressure, for example.

Note that the air holes h1 and h2 are shown only in FIG. 15, and are not shown in other figures.

In FIG. 4, the sub-holding surfaces 12s of the side pads 12 are provided in a pair while being apart from the first main pad 11A in the girth direction X. The sub-holding surface 12s is only required to hold a portion of an area of a non-skin-contact surface 3b of the flap 3 that corresponds to the male touch fastener 4.

Figure 9:
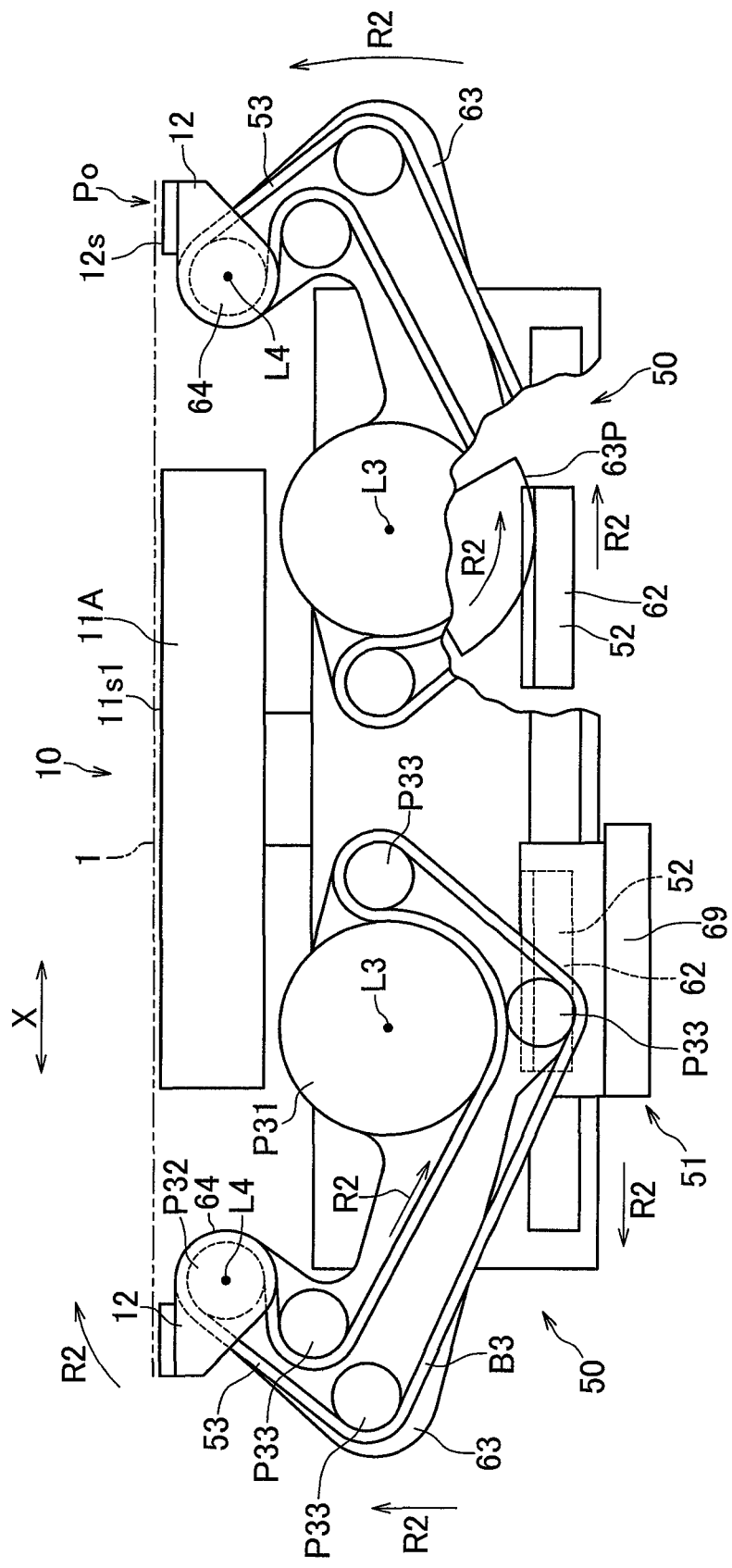
FIG. 9 is a partially-cut-away schematic front view showing a sub-folding mechanism in a sub-open position.
Figure 10:
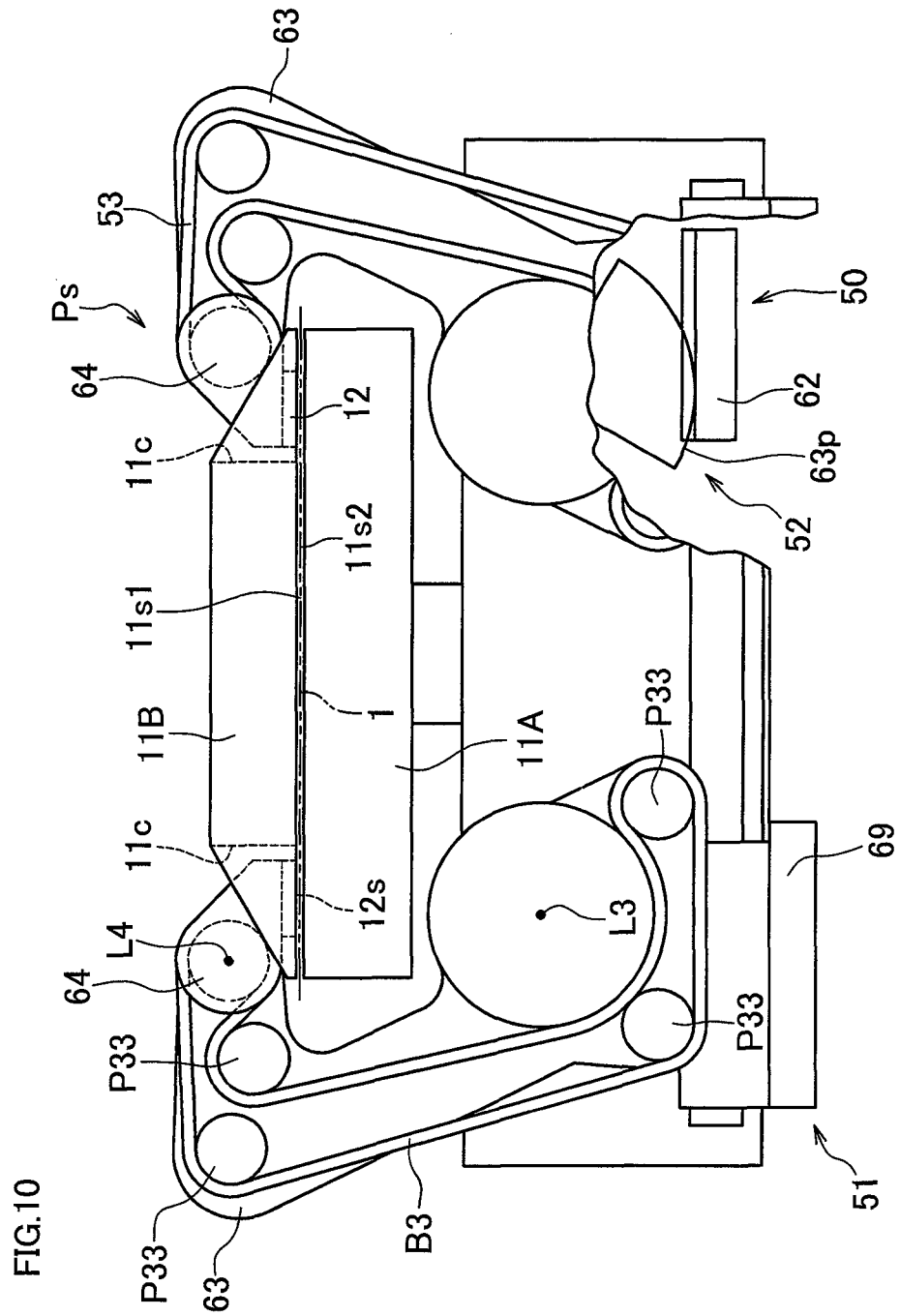
FIG. 10 is a partially-cut-away schematic front view showing a sub-folding mechanism in a sub-closed position.

The sub-folding mechanism 50 of FIG. 9 rotates the side pads 12 with respect to the first main pad 11A from the sub-open position Po where the side pads 12 are open while lying next to the first main pad 11A in the girth direction X to the sub-closed position Ps where the sub-holding surfaces 12s of FIG. 10 are closed while opposing the first holding surface 11s1, thereby folding the flap 3 so that the skin-contact surface 3a of the flap 3 of FIG. 2A lies on the attachment portion 5a of the non-skin-contact surface 2a of the front portion 20.

Cut-outs 11c are formed at positions of the second main pad 11B of FIG. 4 that correspond to the attachment portions 5a. The cut-outs 11c do not allow the attachment portions 5a to be held by the second main pad 11B, but instead expose the attachment portions 5a.

The cut-outs 11c shown in FIG. 10 allow the flaps 3 to be attached to the attachment portion 5a of the front portion 20 of FIG. 1 in the main closed state and in a state where the diaper main body 2 is folded in two at the crotch portion 22. Moreover, the cut-outs 11c allow the side pads 12 to rotate from the sub-open position Po of FIG. 11 to the sub-closed position Ps of FIG. 14, fitting into the cut-outs 11c.

That is, the length Y11 of the cut-out 11c of FIG. 4 in the longitudinal direction Y is greater than the length Y12 of the side pad 12 in the longitudinal direction Y, and in the main closed state of FIG. 10, the side pad 12 is located on the outer side in the girth direction X with respect to an end of the second main pad 11B that defines the cut-out 11c.

In FIG. 1, the second main pad 11B is shown by a phantom line. The cut-outs 11c are formed so that the second main pad 11B shown by the phantom line and the flaps 3 as folded do not lie on each other. More specifically, the cut-out 11c is formed over an area that contains both an area over which the flap 3 and the front portion 20 lie on each other and an area of the side pad 12 in the sub-closed position Ps.

In the case of the present embodiment, the second main pad 11B includes upper end portions 11e for pressing down the left and right upper end portions of the front portion 20.

That is, the cut-out 11c is formed so as to gouge out the edge portion E1 along the longitudinal direction over an area between the upper end portion 11e and the crotch portion 22.

In FIG. 10, the first holding surface 11s1 of the first main pad 11A is present in an area corresponding to the cut-out 11c, and the sub-holding surface 12s of the side pad 12 opposes the first holding surface 11s1 in an area of the cut-out 11c in the sub-closed position Ps of FIG. 10. Note that the air holes h1 (FIG. 15) may be provided also in the upper end portions 11e.

In the present invention, the cut-outs 11c may be formed in areas corresponding to upper-end corners of the front portion 20, without forming the upper end portions 11e in the second main pad 11B.

As shown in FIGS. 7 and 8, the main folding mechanism 40 of FIG. 6 folds the diaper main body 2 by rotating the second main pad 11B with respect to the first main pad 11A so that the second holding surface 11s2 of the second main pad 11B opposes the first holding surface 11s1 of the first main pad 11A.

The main folding mechanism 40 will now be described.

As shown in FIGS. 6 to 8, the main folding mechanism 40 rotates the second main pad 11B with respect to the first main pad 11A to a position such that the second holding surface 11s2 opposes the first holding surface 11s1, and a portion of the second holding surface 11s2 is generally parallel to a portion of the first holding surface 11s1. Each main folding mechanism 40 includes a main arm 13, a main wrist 14, and a main driving mechanism 41 of FIG. 11.

The main arm 13 of FIG. 11 rotates about the first axis L1 extending parallel to the main rotation shaft 91 (FIG. 3). The main wrist 14 rotatably supports the second main pad 11B about the second axis L2 in a tip portion 13A of the main arm 13. The second axis L2 is parallel to the first axis L1. The main driving mechanism 41 of FIG. 5 rotates the main arm 13 and the main wrist 14 in a predetermined rotation direction so as to fold the diaper main body 2.

In FIG. 6, each main driving mechanism 41 includes a main arm rotating mechanism 42 and a main wrist rotating mechanism 43.

The main arm rotating mechanism 42 rotates the main arm 13 about the first axis L1 so that the second main pad 11B moves from the first position P11 of FIG. 6 where it is lying next to the first main pad 11A to the second position P12 of FIG. 8 where it is on the circumferentially outer side of the main pad 11 as the main pads 11 rotate along the conveyance circle C following the rotation of the main rotation shaft 91 of FIG. 3.

On the other hand, the main wrist rotating mechanism 43 of FIG. 11 rotates the second main pad 11B on the main wrist 14 about the second axis L2 following the rotation of the main arm 13 by the main arm rotating mechanism 42. With the rotation of the main wrist 14 and the rotation of the main arm 13, the second main pad 11B rotates to the second position P12 as shown in FIG. 3, and the second holding surface 11s2 of FIG. 8 rotates until it opposes the first holding surface 11s1, thereby folding the diaper main body 2.

Next, a detailed structure of the main arm rotating mechanism 42 will be described.

In FIGS. 3 and 20, a circumferential first cam groove (first cam) 17 shown by a two-dot-chain line is formed on the side surface of the fixed portion 15A fixed to the fixed frame. On the other hand, a rotating member 44 is rotatably supported by the rotating portion 16A for each main arm rotating mechanism 42. A first cam follower 18 is attached to the rotating member 44 at a position that is eccentric with respect to the rotating member 44 of FIG. 5. A pulley P1 is attached coaxially to the rotating member 44.

The rotating member 44 of FIG. 3 rotates about the main rotation shaft 91 together with the rotating portion 16A. During this rotation, the first cam follower 18 swings as it is guided along the first cam groove 17, thereby making the pulley P1 reciprocally rotate together with the rotating member 44.

A main arm rotation shaft 45 of FIG. 11 is rotatably attached to the rotating portion 16A. A pulley P2 and the main arm 13 are attached to one end of the main arm rotation shaft 45. As the pulley P1 of FIG. 5 reciprocally rotates, an endless belt B1, the pulley P2 and the main arm 13 of FIG. 11 swing, thereby making the second main pad 11B reciprocate between the first position P11 and the second position P12 of FIG. 14.

Next, the details of the structure of the main wrist rotating mechanism 43 will be described.

A pulley P3 is provided coaxially with the main arm rotation shaft 45 on the main arm rotation shaft 45 of FIG. 6. The pulley P3 is fixed so as not to rotate with respect to the rotating portion 16B.

A pulley P4 and a pulley P5 are provided on opposite sides of the pulley P3. An endless belt B2 is wound around these pulleys P3 to P5. The pulley P5 is fixed to one end of a rotation shaft 46 forming the main wrist 14. The second main pad 11B is fixed to the rotation shaft 46.

Now, if the pulley P1 of FIG. 5 rotates in the closing direction R1, the belt B1 also rotates in the closing direction R1, thereby making the pulley P2 and the main arm 13 of FIG. 11 rotate in the closing direction R1. On the other hand, since the pulley P3 of FIG. 6 does not rotate, the belt B2 rotates in the closing direction R1 following the rotation of the main arm 13 (FIG. 11), and the pulley P5 rotates in the closing direction R1. Thus, the second main pad 11B of FIG. 11 rotates in the closing direction R1 together with the main wrist 14.

Therefore, the main wrist 14 rotates in the closing direction R1 following the rotation of the main arm 13 in the closing direction R1. Thus, as shown in FIGS. 11 to 14, as the main arm 13 rotates in the closing direction R1, the second main pad 11B and the rotation shaft 46 rotate about the first axis L1 while rotating about the second axis L2. As shown in FIG. 8, the second main pad 11B rotates to an attitude such that a portion of the second holding surface 11s2 is parallel to a portion of the first holding surface 11s1, so that the second holding surface 11s2 opposes the first holding surface 11s1.

Thus, by the rotation, the diaper main body 2 of FIG. 2A is folded.

Note that the action by which the second main pad 11B of FIG. 3 returns from the second position P12 to the first, original position P11 (the opening action) is reverse from the rotation in the closing direction R1, and will not be further described below.

The sub-folding mechanism 50 of FIG. 9 folds the flaps 3 by rotating the pair of side pads 12 with respect to the first main pad 11 so that the sub-holding surfaces 12s of the pair of side pads 12 oppose the first holding surface 11s1 of the first main pad 11A as shown in FIG. 10.

The sub-folding mechanism 50 will now be described.

As shown in FIGS. 9, 10 and 16 to 19, the sub-folding mechanism 50 of FIG. 10 rotates the pair of side pads 12 with respect to the first main pad 11A to a position such that the sub-holding surfaces 12s oppose the first holding surface 11s1 and the sub-holding surfaces 12s are parallel to the first holding surface 11s1. Each sub-folding mechanism 50 includes a sub-arm 63, a sub-wrist 64, and a sub-driving mechanism 51.

Figure 16:
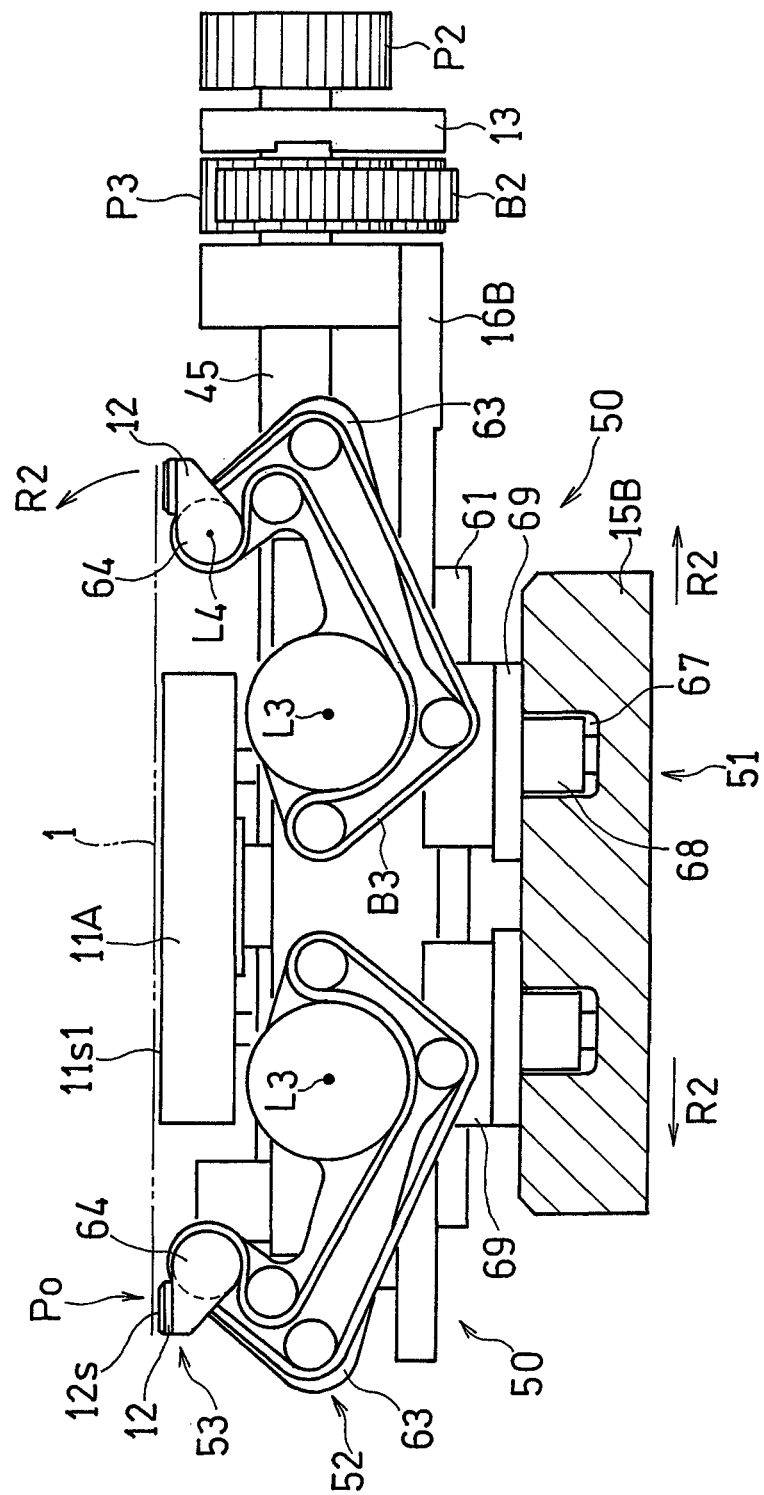
FIG. 16 is a partially-cross-sectional schematic front view showing the folding device in a main open state.
Figure 17:
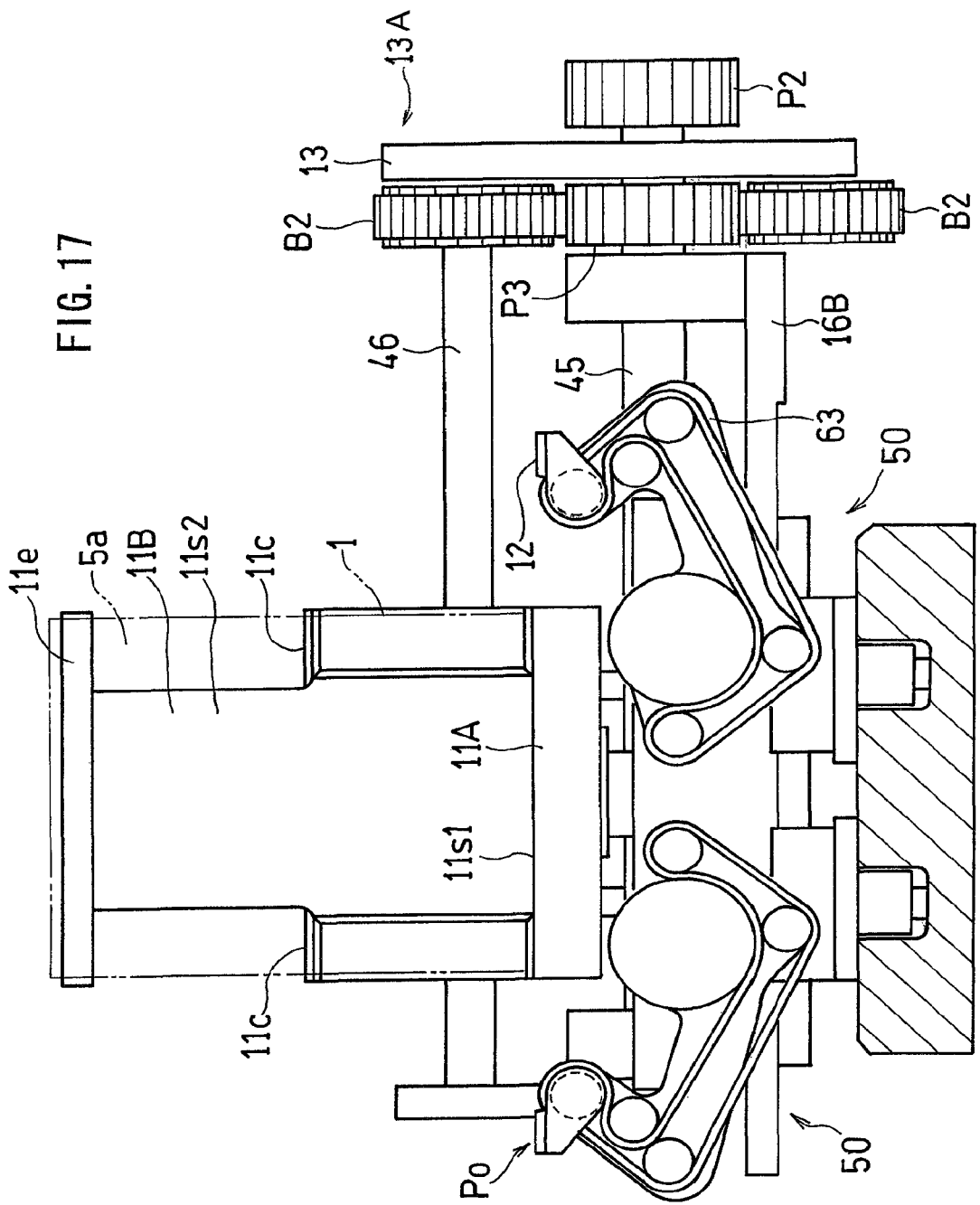
FIG. 17 is a schematic front view showing the folding device in a half open state.

Each sub-arm 63 of FIG. 16 rotates about the third axis L3 extending in the tangential direction to a drum 9 (FIG. 3). The sub-wrist 64 rotatably supports the side pad 12 about the fourth axis L4 in a tip portion of the sub-arm 63. The fourth axis L4 is parallel to the third axis L3. The sub-driving mechanism 51 rotates the sub-arm 63 and the sub-wrist 64 in a predetermined rotation direction so as to fold the flap 3.

Each sub-driving mechanism 51 of FIG. 9 includes a sub-arm rotating mechanism 52, and a sub-wrist rotating mechanism 53. The sub-driving mechanisms 51 have structures that are left-right symmetrical with each other. Hereinafter, one of the sub-arm rotating mechanisms 52 and one of the sub-wrist rotating mechanisms 53 will be discussed.

The sub-arm rotating mechanism 52 rotates the sub-arm 63 about the third axis L3 so that the side pad 12 moves from the sub-open position Po of FIG. 9 where it is lying next to the first main pad 11A to the sub-closed position Ps of FIG. 10 where it is on the circumferentially outer side of the first main pad 11A as the main pads 11 rotate along the conveyance circle C following the rotation of the main rotation shaft 91 (FIG. 3).

On the other hand, the sub-wrist rotating mechanism 53 rotates the side pad 12 on the sub-wrist 64 about the fourth axis L4 following the rotation of the sub-arm 63 by the sub-arm rotating mechanism 52. With the rotation of the sub-wrist 64 and the rotation of the sub-arm 63, the side pad 12 rotates to the sub-closed position Ps and the sub-holding surface 12s of FIG. 18 rotates to oppose the first holding surface 11s1, thereby folding the flap 3, as shown in FIGS. 16 to 19.

Next, the details of the structure of the sub-arm rotating mechanism 52 will be described.

As shown in FIG. 16, a circumferential second cam groove 67 is formed on the outer periphery surface of the fixed portion 15B. On the other hand, a second cam follower 68 to be guided along the second cam groove 67 is provided on the rotating portion 16B for each sub-arm rotating mechanism 52. The second cam follower 68 is attached to a slider 69, and the slider 69 reciprocates along a rail 61 in a direction parallel to the first axis L1 (FIG. 11).

In FIG. 9, a rack 62 is formed integral with the slider 69, and the rack 62 meshes with a pinion 63p of the second arm 63.

The second arm 63 is rotatably supported about the third axis L3. As shown in FIG. 9, the second arm 63 includes a fixed pulley P31 centered about the third axis L3, and a fixed pulley P32 is provided at the fourth axis L4. A belt B3 is wound around the fixed pulley P31 and the fixed pulley P32. Note that P33 is a pulley that meshes with the belt B3.

Now, if the rotating portion 16A (see FIG. 20) of FIG. 3 rotates about the main rotation shaft 91, a pair of sliders 69 move in the closing direction R2 along the rail 61 while being guided along the second cam groove 67 of FIG. 16, as shown in FIGS. 16 to 19. Thus, the rack 62 of FIG. 9 moves in the closing direction R2, and the sub-arm 63 rotates in the closing direction R2 about the third axis L3 together with the pinion 63p.

On the other hand, since the pulley P31 does not rotate, the belt B3 rotates in the closing direction R2 following the rotation of the sub-arm 63, and the pulley P32 rotates in the closing direction R2. Thus, the side pad 12 rotates in the closing direction R2 together with the sub-wrist 64.

Therefore, the sub-wrist 64 rotates in the closing direction R2 following the rotation of the sub-arm 63 of FIG. 9 in the closing direction R2. Thus, as shown in FIGS. 16 to 19, as the sub-arm 63 rotates in the closing direction R2, the side pad 12 rotates about the third axis L3 while rotating about the fourth axis L4. The side pad 12 rotates to an attitude such that the sub-holding surface 12s is parallel to the first holding surface 11s1, and the sub-holding surface 12s opposes the first holding surface 11s1.

Thus, by the rotation, the flaps 3 of the diaper 1 of FIG. 2A are folded as shown in FIG. 2B.

Note that the action by which the side pad 12 of FIG. 10 returns from the sub-closed position Ps back to the original sub-open position Po as shown in FIG. 9 (the opening action) is reverse from the rotation in the closing direction R2, and will not be further described below.

Next, the method for producing diapers 1 from the web W will be described.

As shown in FIG. 2A, the web W is supplied onto the main pad 11 of the folding drum 9 at the pickup position 1P of FIG. 3 in the form of a continuous member including diaper main bodies 2 continuous with one another.

In the angle θ1 including the pickup position 1P, the main pad 11 (11A and 11B) is in the main open state as shown in FIG. 11, and the second main pad 11B is located at the first position P11 in which it is lying next to the first main pad. Therefore, the holding surfaces 11s1, 11s2 and 12s shown in FIG. 11 receive the web W by sucking and holding the web W. In this process, the diaper main body 2 is placed on the first and second holding surfaces 11s1 and 11s2 with the flaps 3 bridging between the first holding surface 11s1 and the sub-holding surface 12s, as shown in FIG. 4, thus holding the flaps 3 on the sub-holding surfaces 12s.

Note that through the angle θ1 of FIG. 3, the diameter of the first cam groove 17 is constant.

As the folding drum 9 of FIG. 3 rotates in this state, the web W being stretched along the conveyance circle C by the main pad 11 and the side pads 12 is severed along the severing line CL of FIG. 2A at the severing position 2P between the pickup position 1P and the folding position 3P, thereby cutting individual diapers 1 out of the web W.

The severed diaper 1 is folded as follows at the folding position 3P of FIG. 3.

In the angle θ2 about the main rotation shaft 91, the diameter of the first cam groove 17 gradually decreases downstream Y. Through the angle θ2, as the folding unit 10 rotates downstream Y, the main arms 13 and the main wrists 14 rotate in the closing direction R1.

Figure 12:
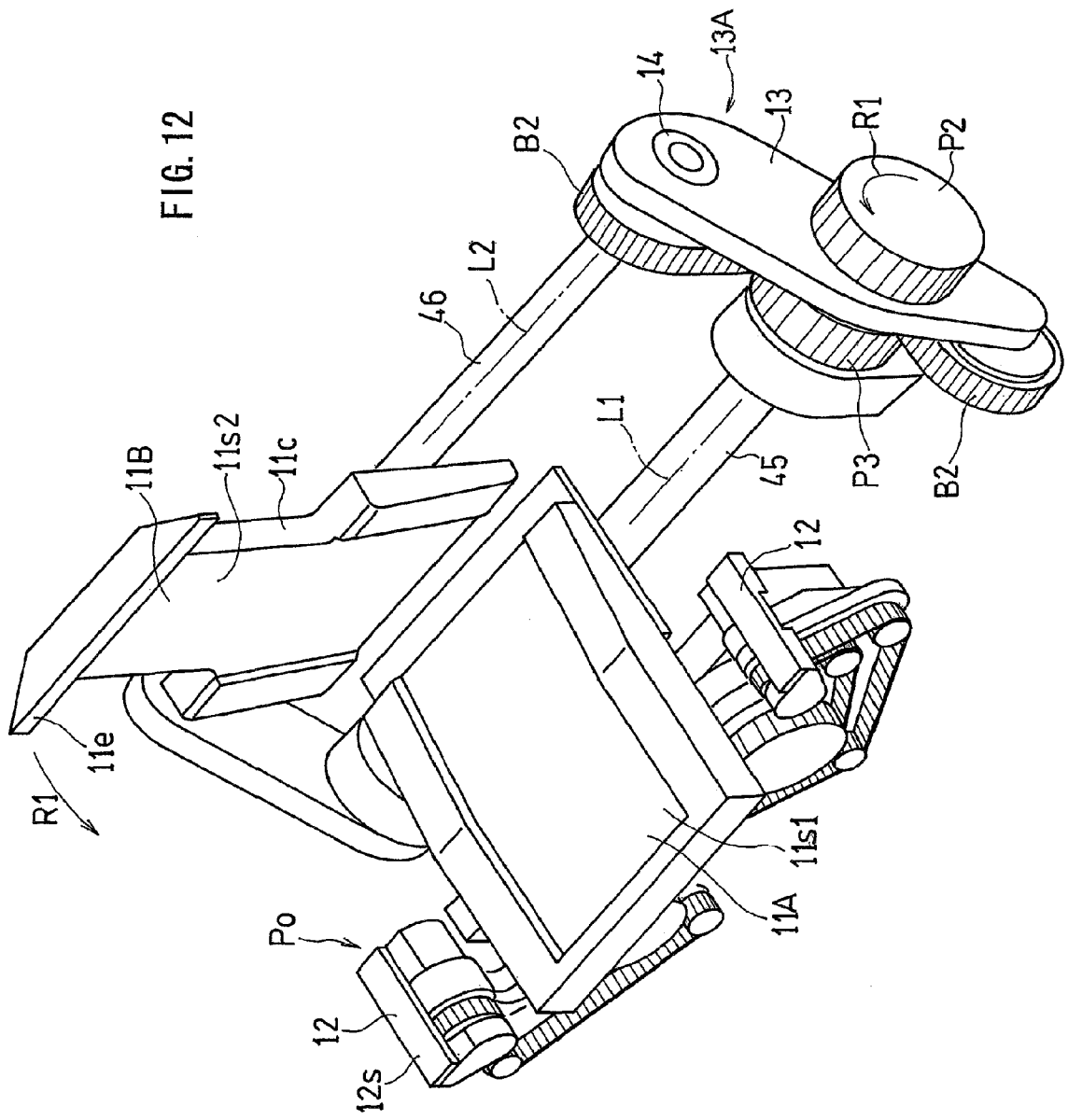
FIG. 12 is a schematic perspective view showing a folding device in a half open state.
Figure 13:
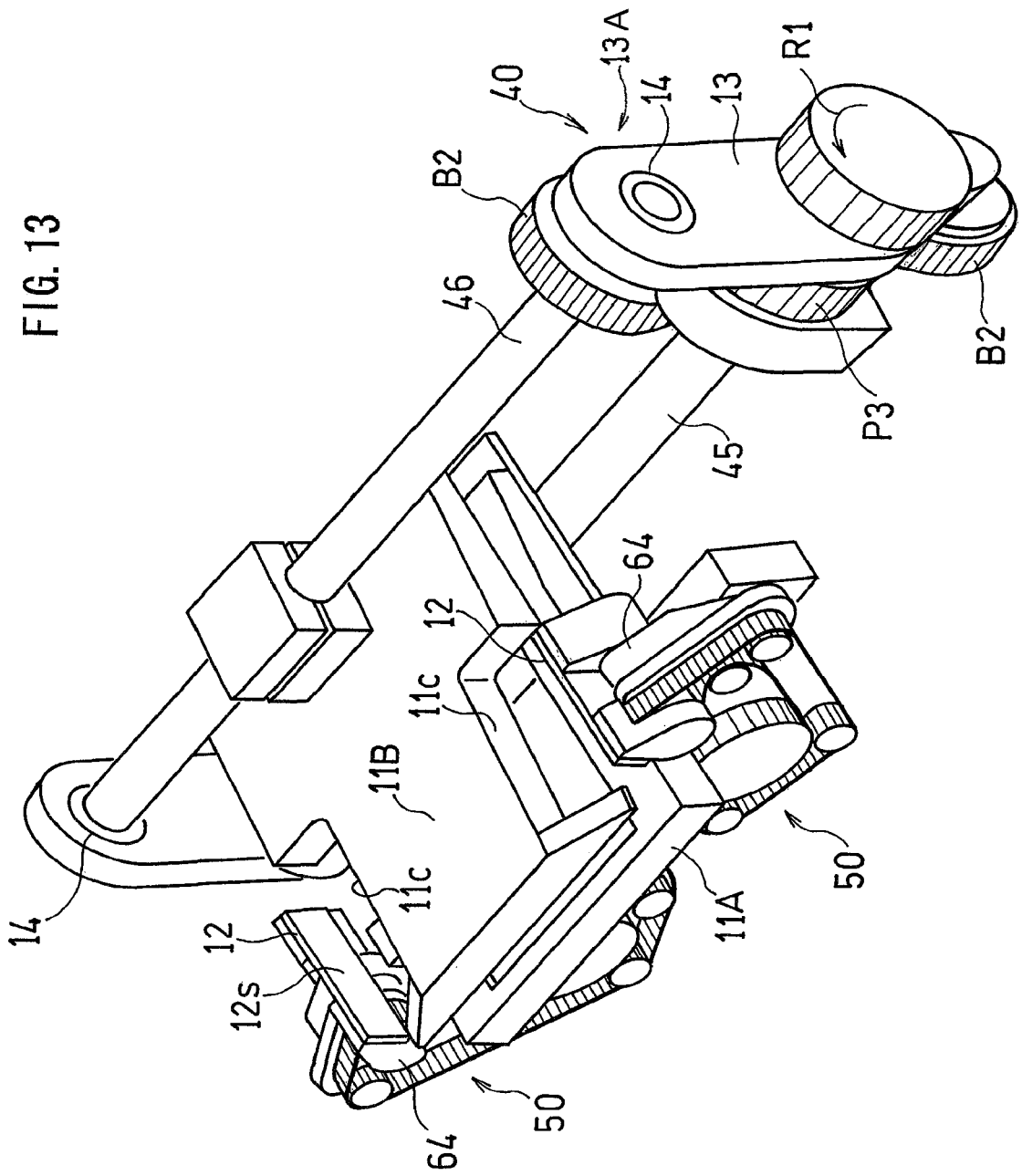
FIG. 13 is a schematic perspective view showing a folding device immediately before the main closed state.
Figure 18:
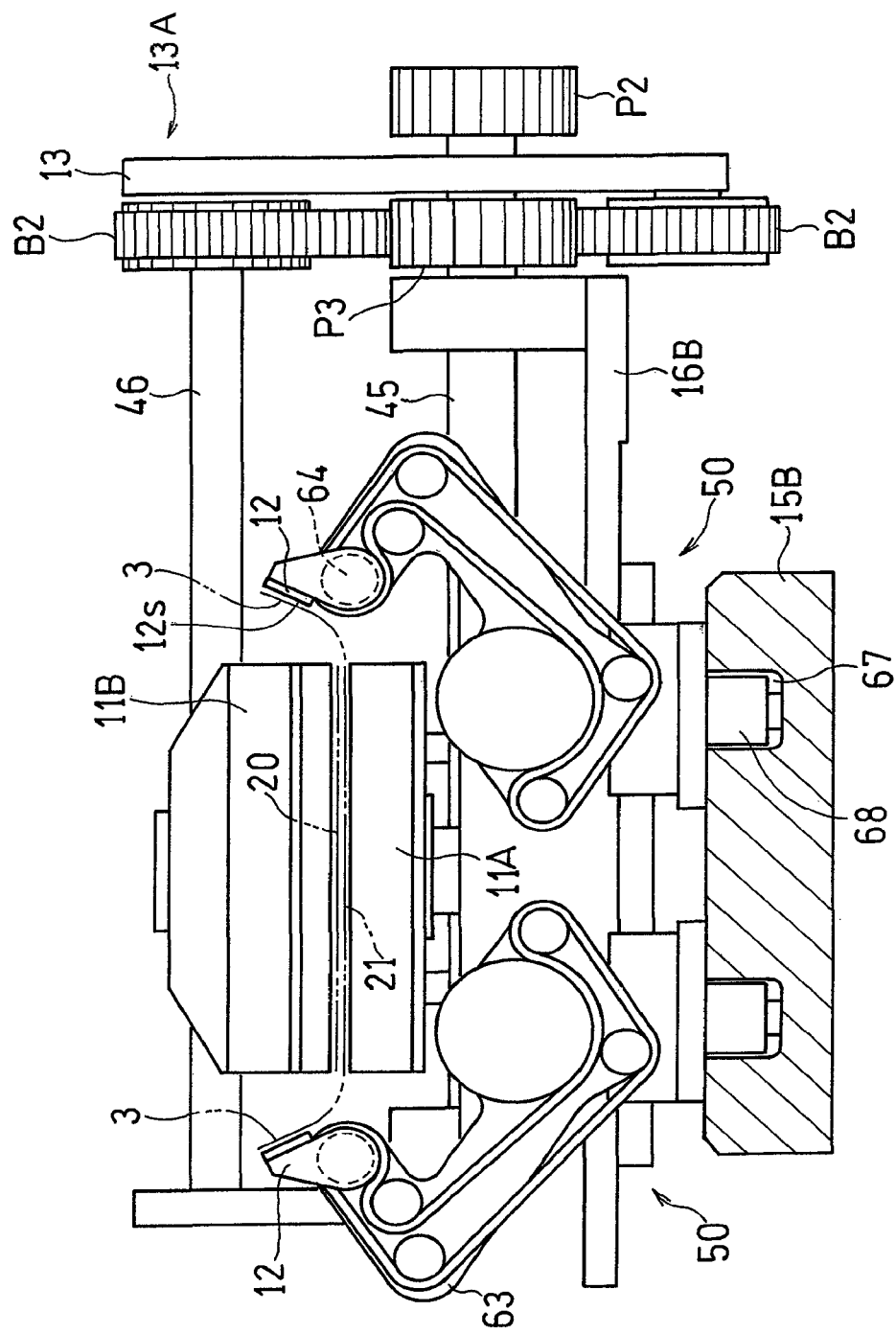
FIG. 18 is a schematic front view showing a folding device immediately before the main closed state.
Figure 19:
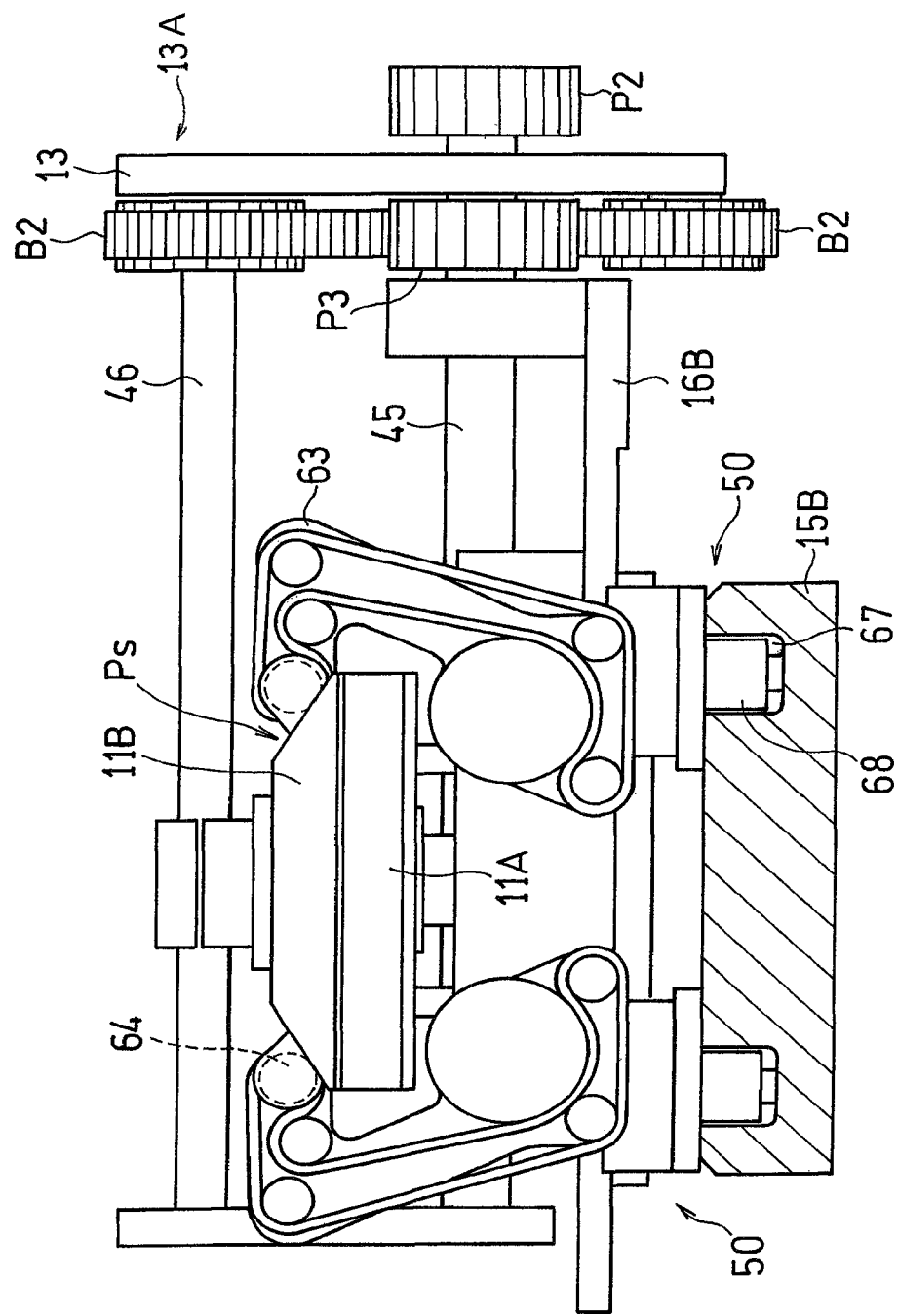
FIG. 19 is a schematic front view showing the folding device in a main closed state, where side pads are in a sub-closed position.

That is, as the folding unit 10 rotates toward the folding position 3P, the first cam follower 18 is guided along the first cam groove 17 so that the main arm 13 rotates in the closing direction R1 and the main wrist 14 of FIG. 12 rotates in the closing direction R1 as described above. As shown in FIGS. 13 and 18, the sub-folding mechanism 50 starts operating immediately before reaching the folding position 3P of FIG. 3.

That is, after the main pad 11 (11A and 11B) starts closing by means of the main folding mechanism 40 and before the main pad 11 reaches the main closed state where it is completely closed by means of the main folding mechanism 40, the pair of side pads 12 start pivoting from the sub-open position Po toward the sub-closed position Ps by means of the sub-folding mechanism.

Moreover, when the folding position 3P of FIG. 3 is reached, the second main pad 11B squarely opposes a portion of the first main pad 11A as a result of the rotation of the main arm 13 and the main wrist 14 (FIG. 11), as shown in FIG. 8, thereby folding the diaper main body 2 in two at the crotch portion 22.

On the other hand, as the sub-arms 63 and the sub-wrists 64 rotate so that the sub-holding surfaces 12s squarely opposes the first holding surface 11s1 as shown in FIG. 10, the flaps 3 are folded and the male touch fastener 4 come into contact with, and engage with, the female touch fastener 5.

That is, with the attachment portions 5a of the front portion 20 being exposed while being not held by the second main pad 11B, and with the diaper main body 2 folded at the crotch portion 22 by the main pads, the side pads 12 holding the flaps 3 rotate with respect to the first main pad 11A toward the exposed attachment portions 5a, thereby folding with the skin-contact surfaces of the flaps 3 lying on the attachment portions 5a.

In this process, as the sub-holding surface 12s and the first holding surface 11s1 squarely oppose each other, the touch fasteners 4 and 5 engage with each other while squarely opposing each other, thus ensuring the engagement between the touch fasteners 4 and 5.

Thus, the diaper main body 2 and the flaps 3 of FIG. 1 are folded, and the folded flaps 3 are fixed to the diaper main body 2 via the male touch fastener 4 and the female touch fastener 5, thereby allowing for suction and holding with the flaps 3 folded.

Figure 14:
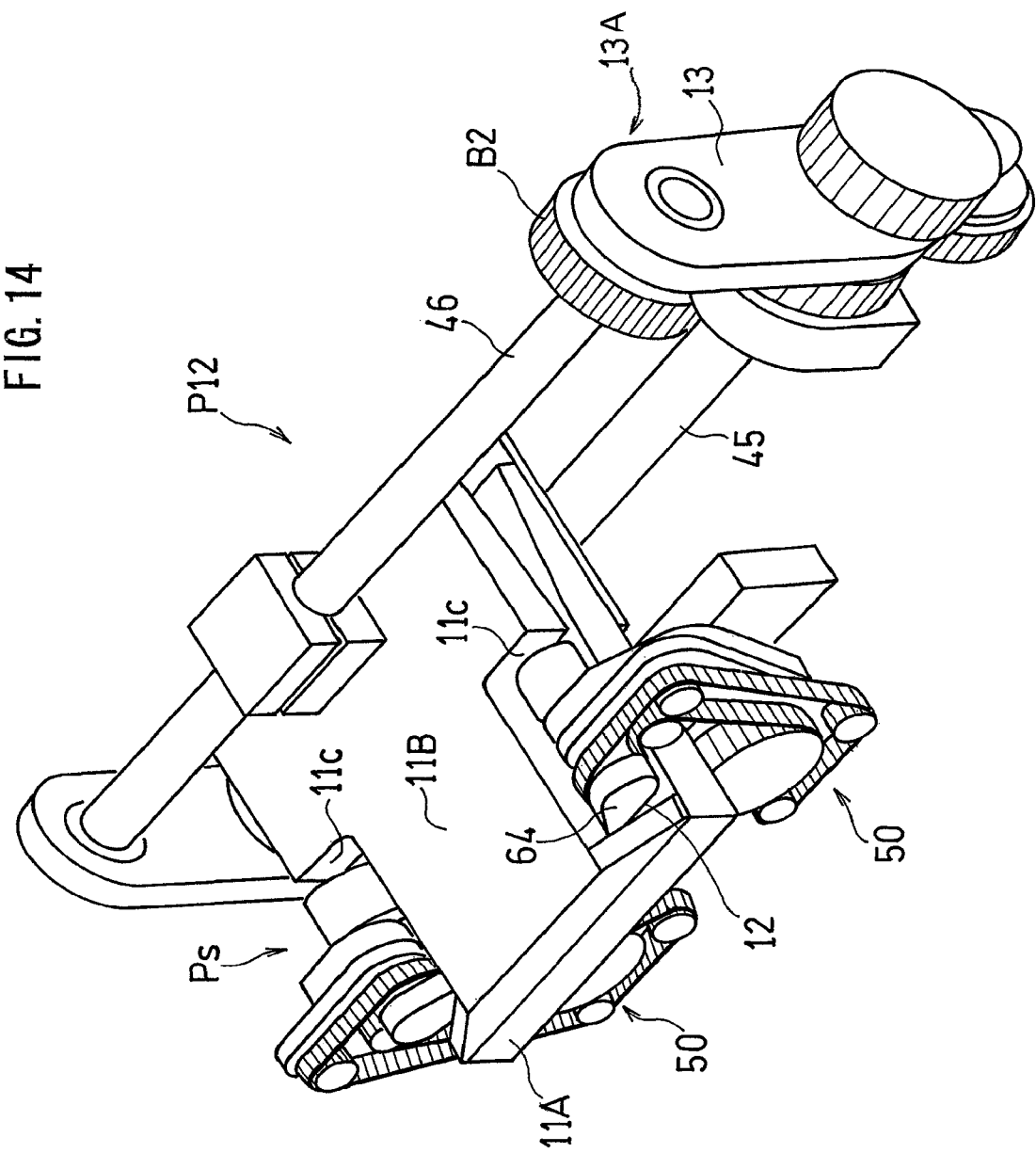
FIG. 14 is a schematic perspective view showing a folding device in a main closed state, where side pads are in a sub-closed position.

Herein, as shown in FIGS. 13 and 14, the cut-outs 11c, which do not allow the attachment portions 5a (FIG. 1) to be held by the second main pad 11B but instead expose the attachment portions 5a (FIG. 1), are formed at positions of the second main pad 11B corresponding to the attachment portions 5a (FIG. 1).

In the main closed state and with the diaper main body 2 folded in two at the crotch portion 22, the cut-outs 11c allow the flaps 3 to be attached to the attachment portions 5a of the front portion 20, and the side pads 12 rotate from the sub-open position Po to the sub-closed position Ps so that the side pads 12 fit into the cut-outs 11c.

The folded state may be maintained through the angle θ3 about the main rotation shaft 91 of FIG. 3. Then, in the angle θ3, the closed arms 13 and 63 (FIG. 14) and the closed wrists 14 and 64 (FIG. 14) rotate in the opening direction.

Note that through the angle θ3, the diameter of the first cam groove 17 gradually increases downstream Y1.

The suction through the air holes h1 and h2 provided in the sub-holding surface 12s and the second holding surface 11s2 of FIG. 15 is released before the arms 13 and 63 (FIG. 14) and the wrists 14 and 64 (FIG. 14) start opening.

After the arms 13 and 63 (FIG. 11) and the wrists 14 and 64 (FIG. 11) open, the diaper 1 is handed over to a conveyer device (not shown) at the hand-over position 4P of FIG. 3. Upon this hand-over, the suction through the air holes h1 provided in the first main pad 11A of FIG. 15 is released.

Note that the folding unit 10 which has handed over the diaper 1 continues to rotate toward the pickup position 1P.

In the present invention, the first main pad may rotate toward the second main pad instead of the second main pad rotating toward the first main pad. Alternatively, both main pads may rotate.

The folding units may be provided on a conveyer instead of on a drum.

While the embodiment above has been directed to the longitudinal flow process where the web is carried in the longitudinal direction, the present invention is also applicable to the so-called "lateral flow process" where the web includes a large number of diapers connected to each other in the girth direction and the web is carried in the girth direction.

In such a case, a cam for folding main bodies may be provided on the outer periphery of the drum, and cams for folding flaps may be provided on the side surfaces of the drum.

The flaps may be integrally continuous with the main body, or may be attached to the main body. That is, the flap encompasses so-called "side panels".

While preferred embodiments have been described above with reference to the drawings, obvious variations and modifications will readily occur to those skilled in the art upon reading the present specification.

For example, a flap may extend out in the girth direction from an edge of the front portion. The diaper may not have the first and second fastener members, and the flaps may be tentatively fastened to the main body by a hot-melt adhesive.

Pads do not need to be sucked by a negative pressure, but a web may be held on pads by piercing a plurality of needles through the web.

The mechanism for rotating the arms and the wrists may be gears instead of belts. Mechanisms for rotating the arms and the wrists may be provided separately from each other.

It is not necessary to rotate both the arms and the wrists as long as the pads are rotated so that the holding surfaces oppose each other.

Note that the pulleys are preferably toothed pulleys, and the belts are preferably timing belts.

Thus, such variations and modifications shall fall within the scope of the present invention as defined by the appended claims.

INDUSTRIAL APPLICABILITY

The present invention is applicable to folding systems for folding main bodies and flaps of worn articles such as disposable diapers.

REFERENCE SIGNS LIST

1: Diaper (an example of a disposable worn article)
2: Diaper body
2a: Skin-contact surface
2b: Non-skin-contact surface
3: Flap
3a: Skin-contact surface
3b: Non-skin-contact surface
4: Male touch fastener
5: Female touch fastener
5a: Attachment portion
9: Folding drum
91: Main rotation shaft
10: Folding unit
11A: First main pad
11B: Second main pad
11s1: First holding surface
11s2: Second holding surface
12: Side pad
12s: Sub-holding surface
13: Main arm
14: Main wrist
17: First cam groove (first cam)
18: Second cam follower
20: Front portion (second torso portion)
21: Back portion (first torso portion)
22: Crotch portion
E1: Edge portion
E2: End portion
L1: First axis
L2: Second axis
30: Severing device
31: Anvil
32: Cutter roller
33: Blade
40: Main folding mechanism
41: Main driving mechanism
42: Main arm rotating mechanism
43: Main wrist rotating mechanism
50: Sub-folding mechanism
51: Sub-driving mechanism
67: Second cam groove (second cam)
68: Second cam follower
X: Girth direction
Y: Longitudinal direction
Y1: Downstream

The invention claimed is:

1. A folding device for a disposable worn article, the disposable worn article comprising: a main body including a first torso portion covering a portion of a torso of a wearer, a second torso portion covering another portion of the torso of the wearer and a crotch portion covering a crotch of the wearer, which are continuous with one another in a longitudinal direction; and a flap being continuous with an edge portion of the first torso portion extending in the longitudinal direction and extending from the edge portion in a girth direction perpendicular to the longitudinal direction so as to be attached to an attachment portion of a non-skin-contact surface of the second torso portion, the folding device comprising:

a first main pad having a first holding surface for holding the first torso portion;

a second main pad having a second holding surface for holding a portion of the second torso portion without holding the attachment portion, the attachment portion exposed;

a main folding mechanism for folding the main body in two at the crotch portion by rotating the first main pad and the second main pad relative to each other so as to transition from a main open state in which the first main pad and the second main pad are open while lying next to each other in the longitudinal direction to a main closed state in which the first holding surface and the second holding surface are closed while opposing facing each other;

a side pad having a sub-holding surface for holding the flap; and a sub-folding mechanism for folding the flap so that a skin-contact surface of the flap lies on the attachment portion of the non-skin-contact surface of the second torso portion by rotating the side pad with respect to the first main pad from a sub-open position in which the side pad is open while lying next to the first main pad in the girth direction to a sub-closed position in which the sub-holding surface is closed while facing the first holding surface, wherein:

the second main pad defines a cut-out, at a position corresponding to the attachment portion, wherein the cut-out exposes the attachment portion without allowing the attachment portion to be held by the second main pad;

in the main closed state and with the main body folded in two at the crotch portion, the cut-out allows the flap to be attached to the attachment portion of the second torso portion, and the side pad rotates from the sub-open position to the sub-closed position, fitting into the cut-out.

2. A folding device according to claim 1, wherein the main folding mechanism rotates the second main pad with respect to the first main pad from the main open state to a position where the second holding surface faces the first holding surface and the second holding surface is parallel to the first holding surface.

3. A folding device according to claim 2, wherein the main folding mechanism comprises: a pair of arms each rotating about a first axis; a wrist for rotatably supporting, in a tip portion of each arm, the second main pad about a second axis parallel to the first axis; and a main driving mechanism for rotating the arm and the wrist in a predetermined rotation direction in order to fold the main body.

4. A folding system comprising a plurality of folding devices according to claim 3 provided on a drum rotating about a main rotation shaft, wherein the first holding surface is provided along a conveyance circle centered about the main rotation shaft, the main driving mechanism comprising:

an arm rotating mechanism for rotating the pair of arms about the first axis so that the second main pad moves from a first position where the second main pad is lying next to the first main pad to a second position where the second main pad is on a circumferentially outer side of the first main pad, as the first holding surface rotates on the conveyance circle following the rotation of the main rotation shaft; and a wrist rotating mechanism for rotating the second main pad on the wrist about the second axis following the rotation of the arms by the arm rotating mechanism.

5. A folding system comprising a plurality of folding devices according to claim 1 along an outer periphery of a drum rotating about a main rotation shaft, the folding system comprising:

a first cam provided on a side surface of the drum;
a first cam follower guided along the first cam; and
a main driving mechanism for driving the main folding mechanism as the first cam follower circles along the first cam.

6. A folding system according to claim 5, wherein:
a pair of the side pads and a pair of the sub-folding mechanisms are provided for each first main pad, wherein the folding system comprises:
a pair of second cams provided on the outer periphery surface of the drum;
second cam followers guided along the second cams; and
a sub-driving mechanism for driving each of the sub-folding mechanisms as each of the second cam followers circle along each of the second cams.

7. A folding device according to claim 1, wherein a first fastener member is provided on the skin-contact surface side of the flap to be folded, and a second fastener member is provided on a non-skin-contact surface of the second torso portion, on which the folded flap lies, and the second fastener member engages with the first fastener member.

8. A folding method for a disposable worn article, the disposable worn article comprising: a main body including a first torso portion covering a portion of a torso of a wearer, a second torso portion covering another portion of the torso of the wearer and a crotch portion covering a crotch of the wearer, which are continuous with one another in a longitudinal direction; and a flap being continuous with an edge portion of the first torso portion extending in the longitudinal direction and extending from the edge portion in a girth direction perpendicular to the longitudinal direction so as to be attached to an attachment portion of a non-skin-contact surface of the second torso portion, the method comprising the steps of:
holding the first torso portion by a first main pad, holding the second torso portion by a second main pad without the attachment portion being held and with the attachment portion exposed, and holding the flap by a side pad;
folding the main body at the crotch portion by rotating at least one of the first main pad and the second main pad, without the attachment portion of the second torso portion being held by the second main pad and with the attachment portion exposed, and so that a skin-contact surface of the first torso portion and a skin-contact surface of the second torso portion lie on each other, face each other, and are in contact with each other; and
folding a skin-contact surface of the flap onto the attachment portion by rotating the side pad holding the flap with respect to the first main pad toward the exposed attachment portion, without the attachment portion of the second torso portion being held by the second main pad and with the attachment portion exposed and with the main body folded at the crotch portion by the main pads.

9. A folding device for a disposable worn article, the disposable worn article comprising: a main body portion including a first torso portion covering a portion of a torso of a wearer, a second torso portion covering another portion of the torso of the wearer and a crotch portion covering a crotch of the wearer, which are continuous with one another in a longitudinal direction, the folding device comprising:
a first main pad having a first holding surface for holding the first torso portion;
a second main pad having a second holding surface for holding the second torso portion; and
a main folding mechanism for folding the main body in two at the crotch portion by rotating the second main pad with respect to the first main pad so as to transition from a main open state in which the first main pad and the second main pad are open while lying next to each other in the longitudinal direction to a main closed state in which the first holding surface and the second holding surface are closed while facing each other,
wherein the main folding mechanism comprises: a pair of arms each rotating about a same first axis; a wrist for rotatably supporting, in a tip portion of each arm, the second main pad about a second axis parallel to the first axis; and a main driving mechanism for rotating the arm and the wrist in a predetermined rotation direction in order to fold the main body.

10. A folding system comprising a plurality of folding devices according to claim 9 provided on a drum rotating about a main rotation shaft, wherein the first holding surface is provided along a conveyance circle centered about the main rotation shaft, the main driving mechanism comprising:
an arm rotating mechanism for rotating the arm about the first axis so that the second main pad moves from a first position where the second main pad is lying next to the first main pad to a second position where the second main pad is on a circumferentially outer side of the first main pad, as the first holding surface rotates on the conveyance circle following the rotation of the main rotation shaft; and
a wrist rotating mechanism for rotating the second main pad on the wrist about the second axis following the rotation of the arm by the arm rotating mechanism.

11. A folding system according to claim 10, wherein the main folding mechanism rotates the second main pad with respect to the first main pad to a position where the second holding surface opposes the first holding surface and the second holding surface is parallel to the first holding surface.

* * * * *